(12) United States Patent
Vetter

(10) Patent No.: US 9,241,691 B2
(45) Date of Patent: Jan. 26, 2016

(54) METHODS AND DEVICES FOR REMOVING TISSUE FROM A PATIENT AND PLACING A MARKER IN THE PATIENT

(75) Inventor: James W. Vetter, Portola Valley, CA (US)

(73) Assignee: ENCAPSULE MEDICAL, LLC, San Francisco, CA (US)

( * ) Notice: Subject to any disclaimer, the term of this patent is extended or adjusted under 35 U.S.C. 154(b) by 0 days.

(21) Appl. No.: 13/345,555

(22) Filed: Jan. 6, 2012

(65) Prior Publication Data
US 2012/0109174 A1 May 3, 2012

Related U.S. Application Data

(63) Continuation of application No. 11/600,929, filed on Nov. 16, 2006, now Pat. No. 8,105,243.

(51) Int. Cl.
*A61B 10/00* (2006.01)
(52) U.S. Cl.
CPC .................................. *A61B 10/0041* (2013.01)

(58) Field of Classification Search
USPC .................................................. 600/562–568
See application file for complete search history.

(56) References Cited

U.S. PATENT DOCUMENTS

| | | | | |
|---|---|---|---|---|
| 5,762,069 | A * | 6/1998 | Kelleher et al. | 600/564 |
| 5,980,469 | A * | 11/1999 | Burbank et al. | 600/567 |
| 6,068,603 | A * | 5/2000 | Suzuki | 600/565 |
| 6,110,127 | A * | 8/2000 | Suzuki | 600/565 |
| 6,322,522 | B1 * | 11/2001 | Zimmon | 600/565 |
| 2004/0059254 | A1 * | 3/2004 | Pflueger | 600/565 |
| 2006/0149163 | A1 * | 7/2006 | Hibner et al. | 600/566 |
| 2006/0224082 | A1 * | 10/2006 | Vetter et al. | 600/564 |
| 2007/0088199 | A1 * | 4/2007 | Ito et al. | 600/156 |

* cited by examiner

*Primary Examiner* — Brian Szmal
*Assistant Examiner* — Megan Leedy

(57) ABSTRACT

The device is used to remove tissue from a patient and to also place a marker in the patient. The device has an opening through which tissue enters the device. The tissue which enters the opening is cut and the tissue is removed. The device may be used a number of times to remove a number of tissue masses. The device also includes a marker which the user may release in the patient at the desired time.

12 Claims, 36 Drawing Sheets

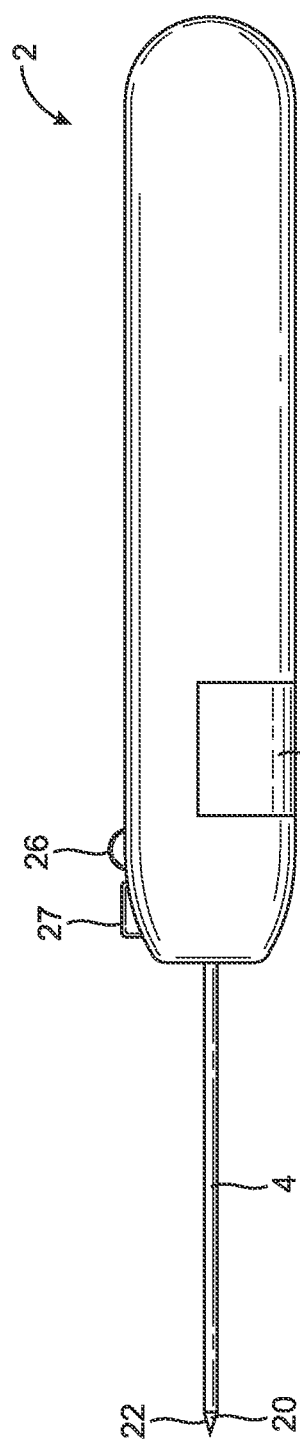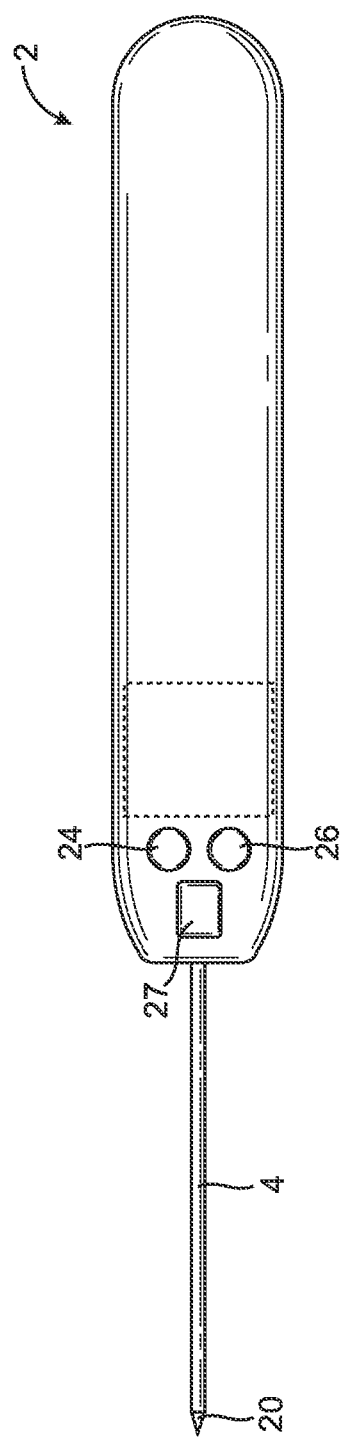

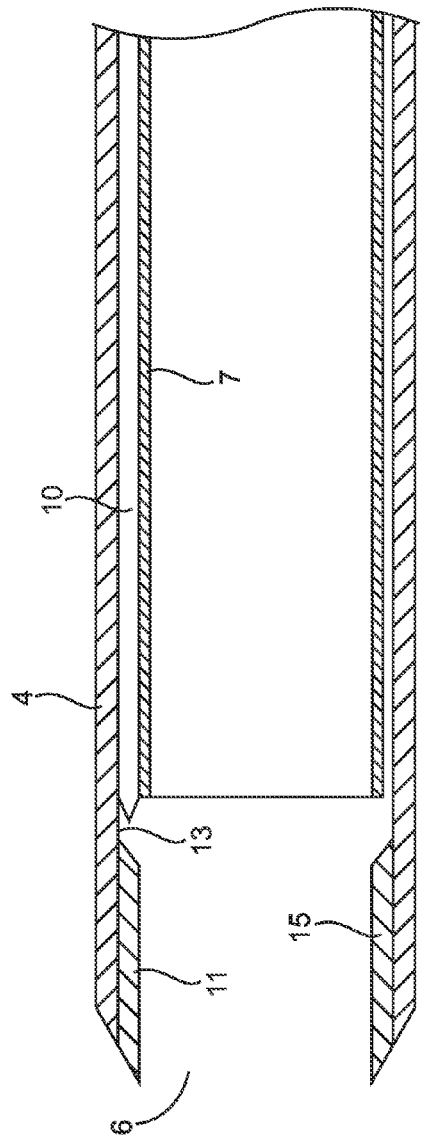
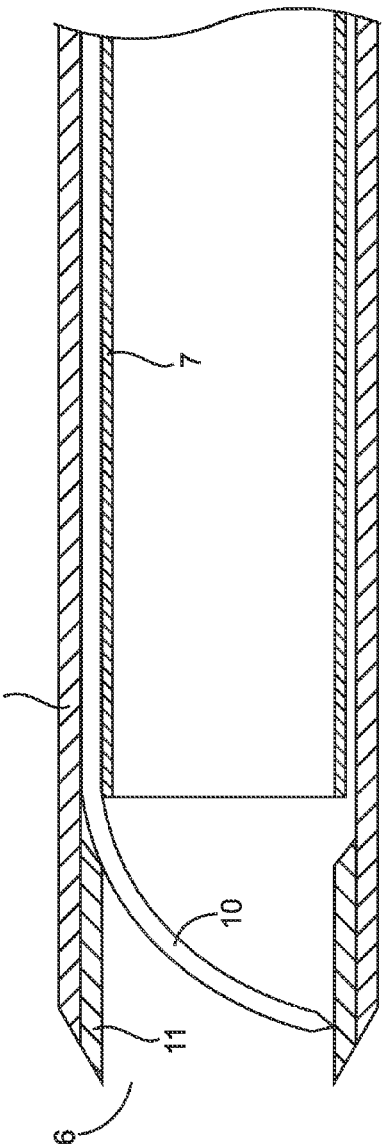

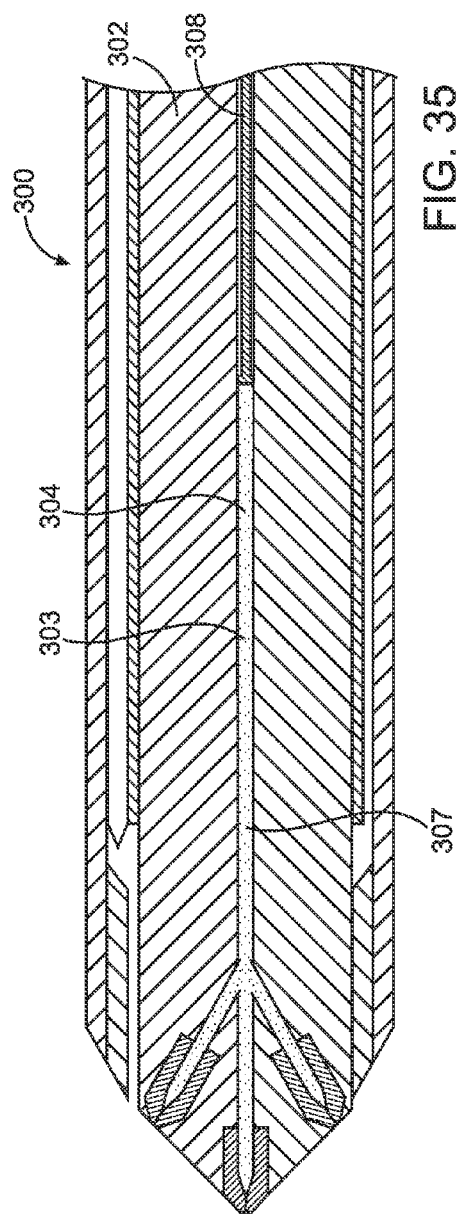
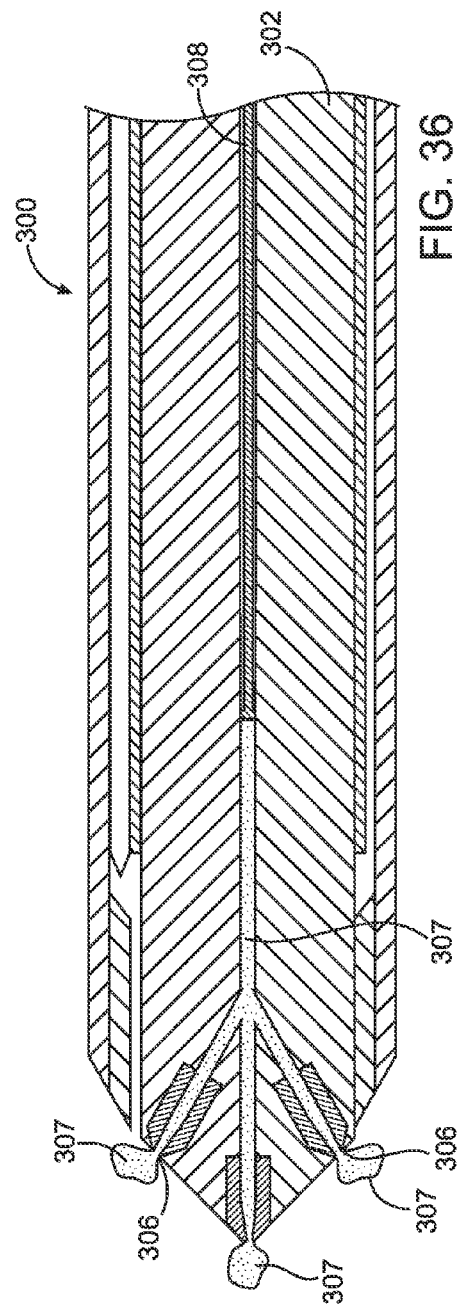

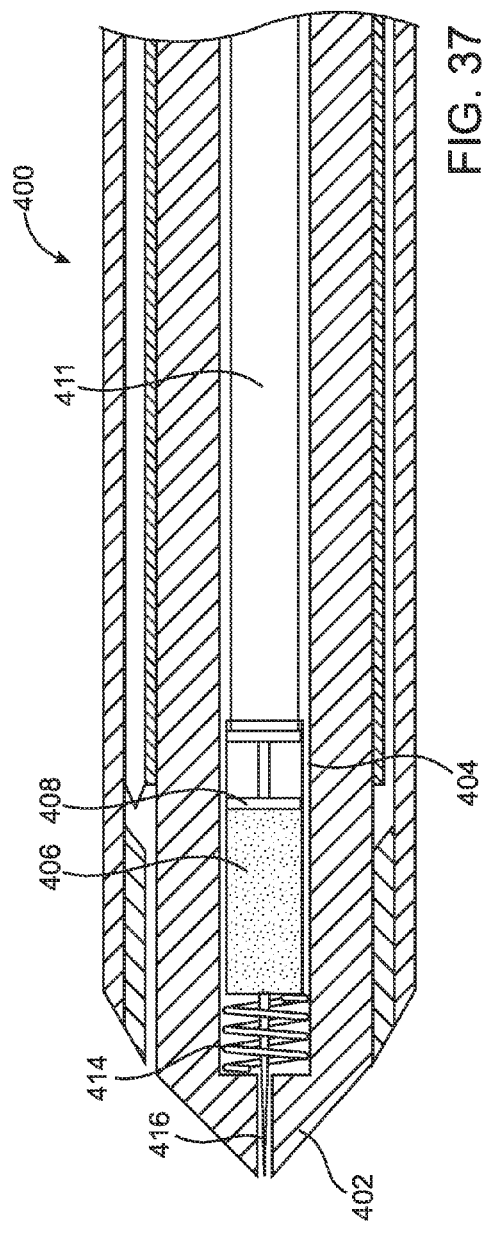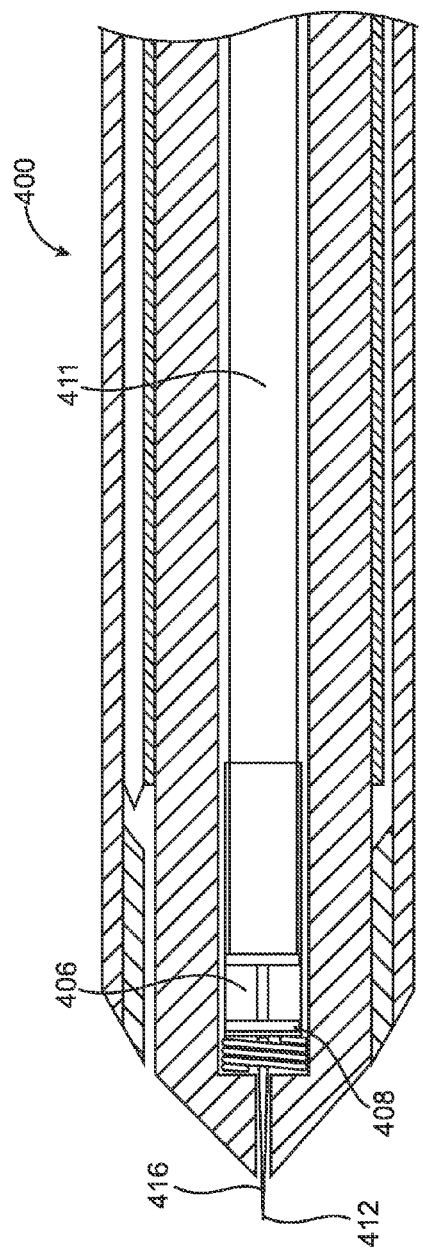

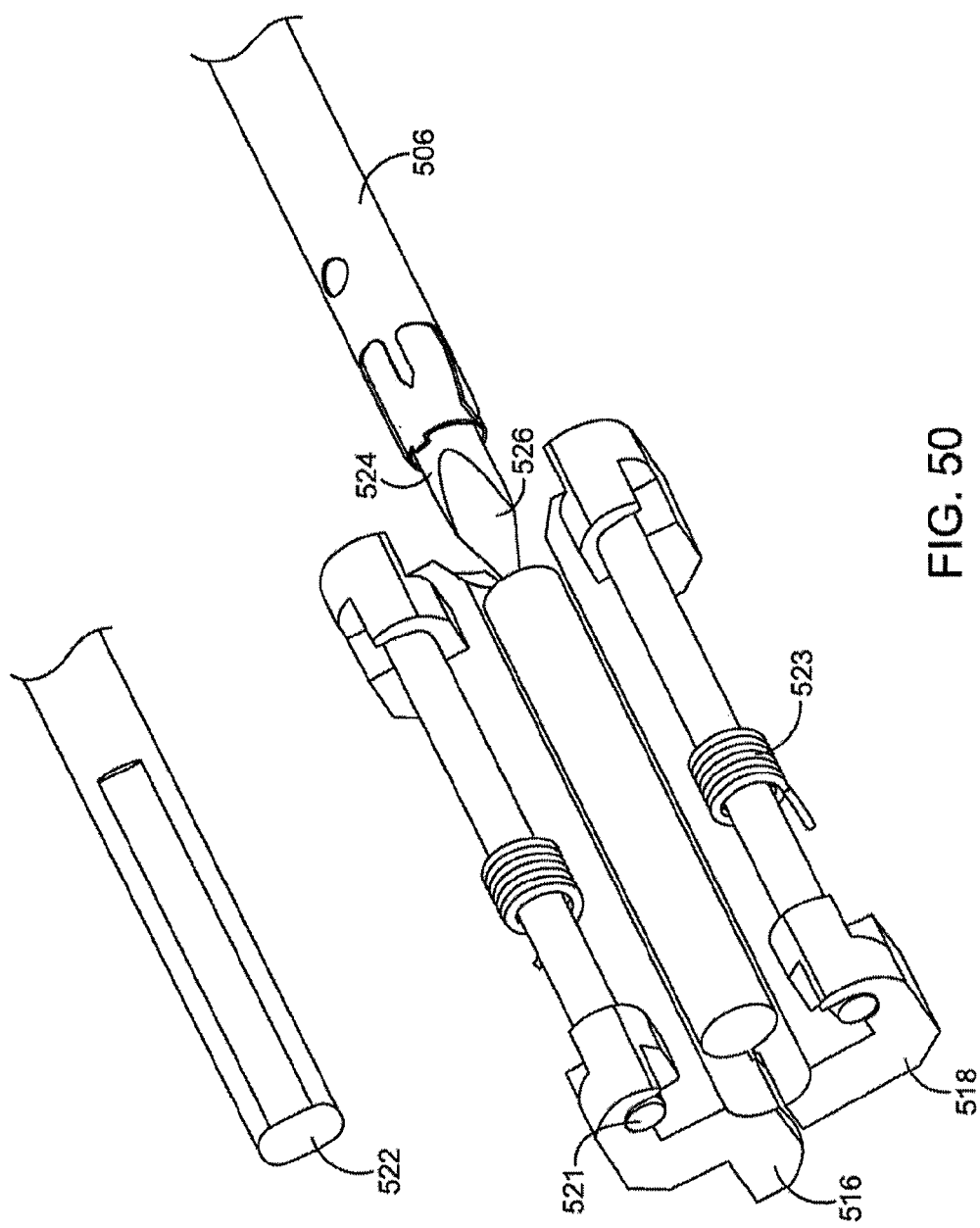

METHODS AND DEVICES FOR REMOVING TISSUE FROM A PATIENT AND PLACING A MARKER IN THE PATIENT

This application is a continuation of application Ser. No. 11/600,929 filed on Nov. 16, 2006, now U.S. Pat. No. 8,105,243 now allowed. The entire disclosure of which is hereby incorporated by reference for all intents and purposes.

BACKGROUND

The present invention is directed to tissue removing devices and methods. The invention may be used to remove tissue from any part of the body and is particularly useful in removing tissue from the breast. Of course, the invention may be used in any other part of the body and use in the breast is merely exemplary.

SUMMARY

In a first aspect of the present invention, a tissue removal device is provided which has a tubular element, a transport element and a cutting element. The tubular element has an open distal end. The transport element and the cutting element are positioned at least partially within the tubular element and are movable within the tubular element. The device is introduced into a patient and the tubular element is advanced so that tissue enters the tubular element through the open end. The cutting element is then used to cut or part-off the tissue which has entered the tubular element and the transport element is used to transport the tissue proximally to a tissue chamber.

The transport element may take many forms. In one embodiment, the transport element has an open end positioned proximal to the open end of the tubular element so that tissue enters the open end of the transport element when the tubular element is advanced into tissue. The transport element may also pierce the tissue being removed from the patient. Furthermore, the transport element may have a deployable anchor which secures the tissue to the transport element. The anchor may take any suitable shape such as deployable barbs, wires or an inflatable balloon.

In another aspect of the present invention, the device may include a cutting element which parts off the tissue which enters the tubular element and also transports the tissue to the tissue chamber. The cutting element may have a first part and a second part which move toward one another to a cutting position when cutting the tissue within the tubular element. The cutting element may be plastically or elastically deformed when moving to a cutting position.

In another aspect of the present invention, devices and methods for removing tissue and placing a marker within the patient are described. The device includes an opening through which tissue is introduced into the device. The tissue is then cut to separate a tissue mass from the surrounding tissue. The device also includes a solid marker housed within the device. The marker may be implanted into the patient at any time desired by the user. The marker may be delivered through the same opening through which tissue is removed or the device may include a separate opening for delivering the marker. The marker may be mounted to the introducer, stored in a storage area in the handle, or may even be stored at a location distal to the opening through which tissue is removed.

In still another aspect of the present invention, a method of removing tissue and marking a tissue area is provided in which the tissue marking element delivers a flowable material. The tissue marking element may have a plurality of outlets to form a recognizable pattern to help locate and orient the tissue area of interest at a later time when the flowable marking material is visualized. The tissue marking element may be advanced through the lumen of the tubular element until an outlet of the tissue marking element is positioned distal to the opening in the tubular element. The tissue marking element may also be part of the introducer with the introducer having one or more outlets through which the flowable substance is delivered.

These and other aspects of the present invention shall become apparent from the following description, drawings and claims.

DESCRIPTION OF DRAWINGS

FIG. 1 shows a tissue removing device in accordance with the present invention.
FIG. 2 shows another view of the device of FIG. 1.
FIG. 3 is a cross-sectional view of a distal end of the tissue removal device with a cutting element in a stored position.
FIG. 4 is a cross-sectional view showing the cutting element in a cutting position.

FIG. 35 shows yet another device for removing tissue and marking a tissue area with an introducer having an outlet through which a flowable marker is delivered.

FIG. 36 shows the device of FIG. 35 with the flowable material delivered.

FIG. 37 shows still another device for removing tissue and marking a tissue area.

FIG. 38 shows a tissue marking element moved to a working position within an introducer.

FIG. 50 is a perspective view of the tissue handling with the tissue contained within the recess and the support member omitted for clarity.

DESCRIPTION OF THE PREFERRED EMBODIMENTS

Figure 5:
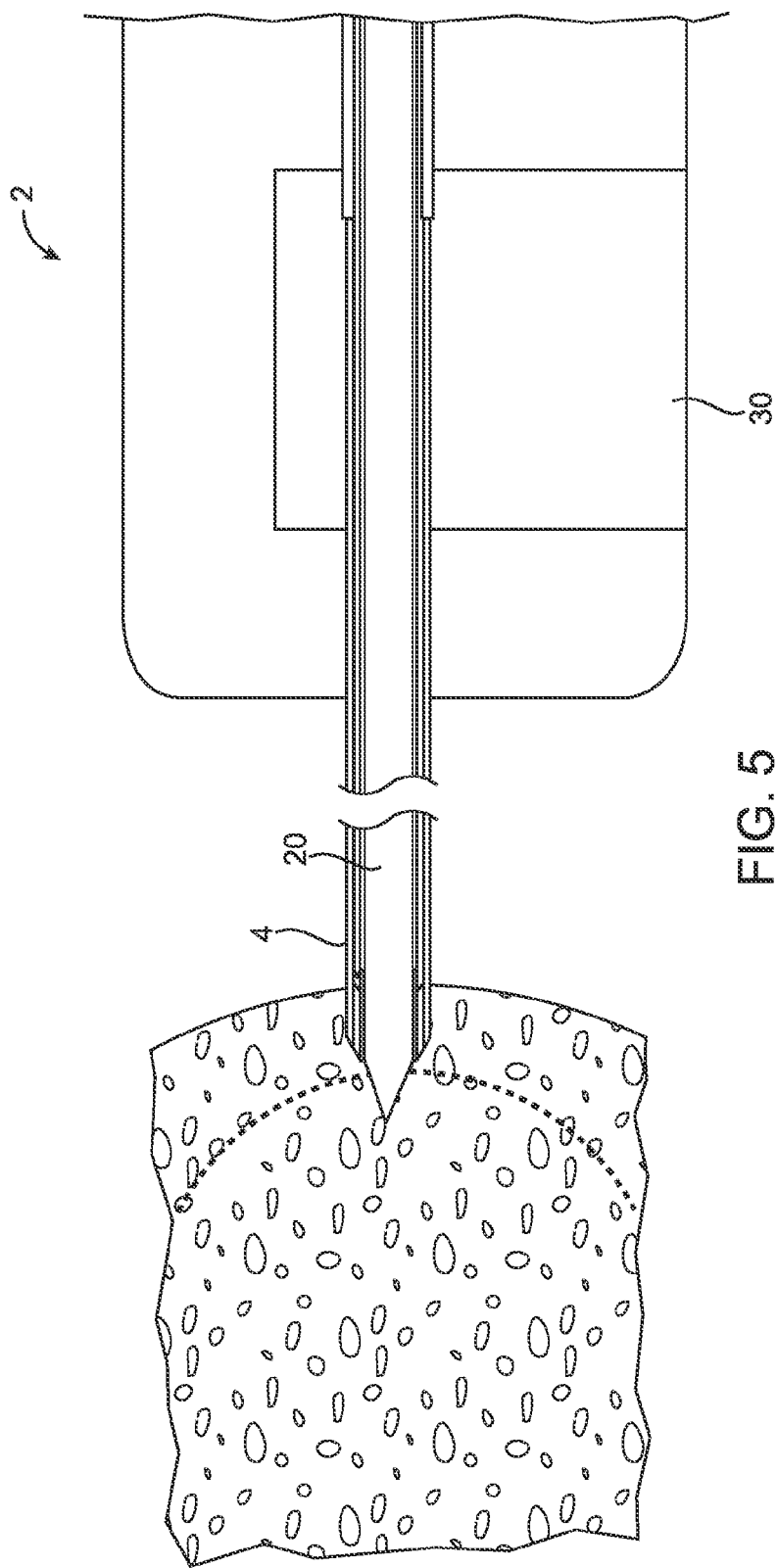
FIG. 5 shows the device being introduced into tissue.

Referring to FIGS. 1-11, a tissue removing device 2 according to the present invention is shown. The devices and methods described herein may be used to remove tissue from any location in the body and an example of such a use is removal of tissue from the breast as described below. The tissue removal device 2 has a tubular element 4 which is advanced into tissue so that tissue is received through an open end 6 of the tubular element 4. A transport element 7 is positioned within the tubular element 4 and is used to transport tissue back to a tissue sample chamber 30 as described below.

The distal end of the tubular element 4 is beveled to form a sharp tip 11 but may take any other suitable configuration which penetrates tissue. The tubular element 4 may also be rotated when driven into the tissue. The tubular element 4 may be made of any suitable material such as stainless steel. The device 2 may also include an introducer 20 positioned in the tubular element 4 during introduction. The introducer 20 may have a sharp tip 22 which penetrates the tissue during introduction of the device 2 as shown in FIG. 5. The device 2 may also be introduced through a sheath, trocar or cannula (not shown) which penetrates the tissue rather than using the device 2 itself to penetrate the tissue.

Although the present invention may be used to collect tissue of any size, the invention is particularly useful in removing relatively small quantities of tissue such as required in breast biopsies. When used for this purpose, the inner diameter of the device 2 may be less than 5 mm or even less than 3.5 mm. The present invention provides the ability to obtain small, cylindrical tissue samples which are relatively undisturbed compared to many prior art solutions. The tubular element 4 may be driven forward a distance of 15-25 mm which may be selected by the user.

The tissue removal device 2 also has a cutting element 10 which is used to cut or "part off" tissue which has entered the tubular element 4 from the surrounding tissue. The cutting element 10 is stored between the tubular element 4 and the transport element 7 and naturally assumes the position of FIG. 4 when advanced. The cutting element 10 also contacts a protrusion 11 on an inner surface 13 of the tubular element 4 which directs the cutting element 10 into the cutting position of FIG. 4. The protrusion 11 may simply be a ring 15 of material attached to the inner surface of the tubular element 4 although any other structure may be used. The transport element 4 and cutting element 10 are then moved proximally to the tissue chamber with the cutting element 10 remaining in the cutting position of FIG. 4 as explained below.

The tissue removal device 2 has a first actuator 24 and a second actuator 26 which are described further below in connection with use of the device 2. Of course, fewer actuators may be used if the function of the actuators can be combined. When the first actuator 24 is depressed, the introducer 20 is retracted proximally to the position shown in FIG. 6 so that the open end of the tubular element 4 is exposed to receive tissue. When the second actuator 26 is depressed, the tubular element 4 is driven forward so that tissue enters the open end 6. The cutting element 10 is then automatically advanced to part off tissue which has entered the open end 6 and the transport element 7 then transports the tissue to the tissue chamber 30. The first and second actuators 24, 26 may be knobs, buttons, levers or triggers and FIGS. 1 and 2 show the first and second actuators 24, 26 being buttons.

Figure 6:
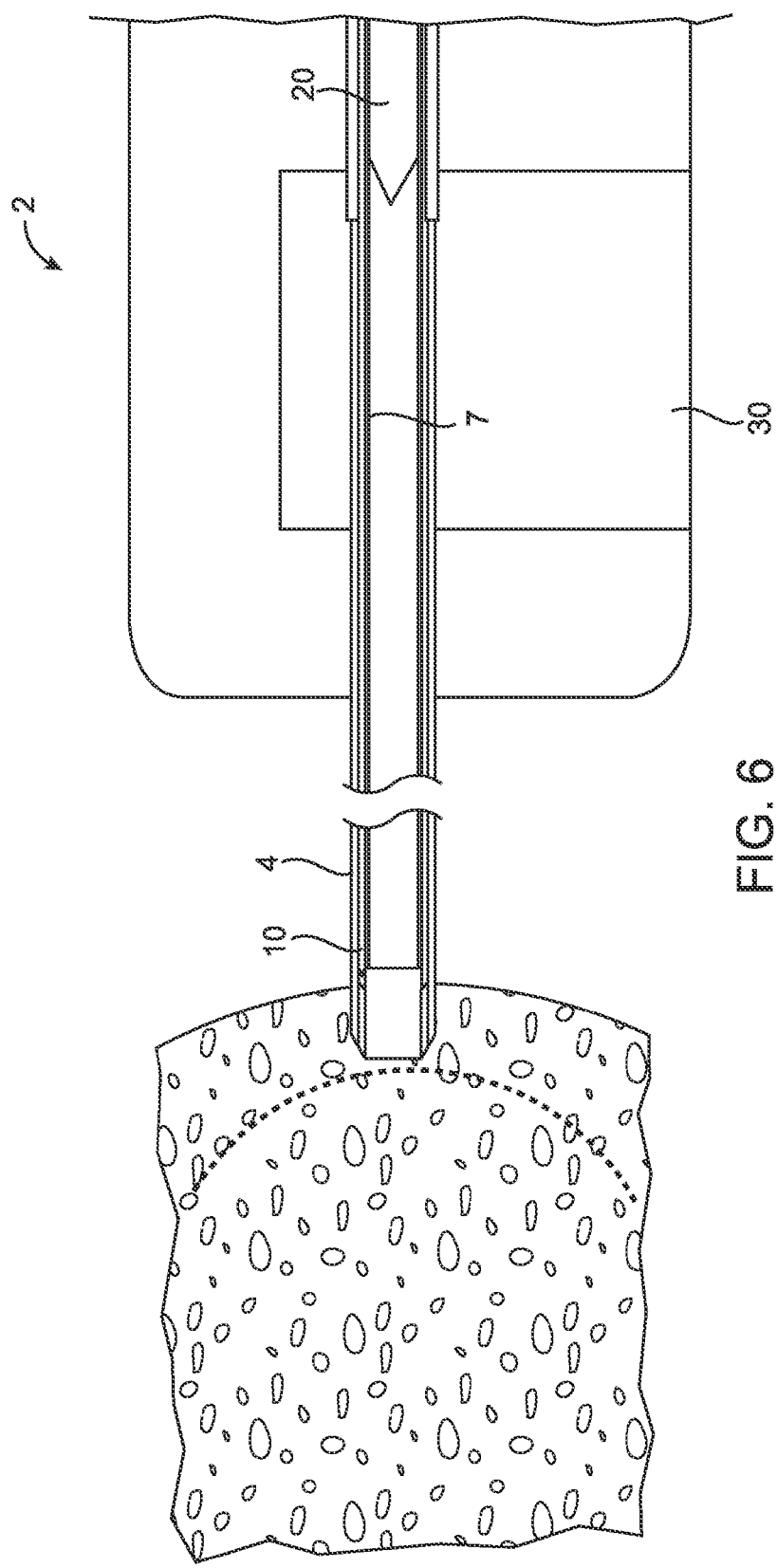
FIG. 6 shows an introducer withdrawn from the distal end.

Use of the tissue removal device 2 is now described in connection with FIGS. 5-11. The device 2 is introduced into the patient for removal of tissue such as breast tissue in a breast biopsy procedure. The device 2 is introduced directly into the tissue with the sharp tip 22 of the introducer 20 penetrating tissue as shown in FIG. 5. The device 2 may also be introduced into the patient through a sheath, trocar or cannula (not shown). Once the distal end is positioned proximal to the tissue to be removed, the first actuator 24 is depressed to withdraw the introducer 20 and expose the open end 6 as shown in FIG. 6. After retracting the introducer 20 the user may, of course, manipulate the device 2 as necessary so that the device 2 is directed toward the tissue to be removed. The introducer 20 may be withdrawn to a position proximal to the tissue chamber 30 or another suitable position.

Figure 7:
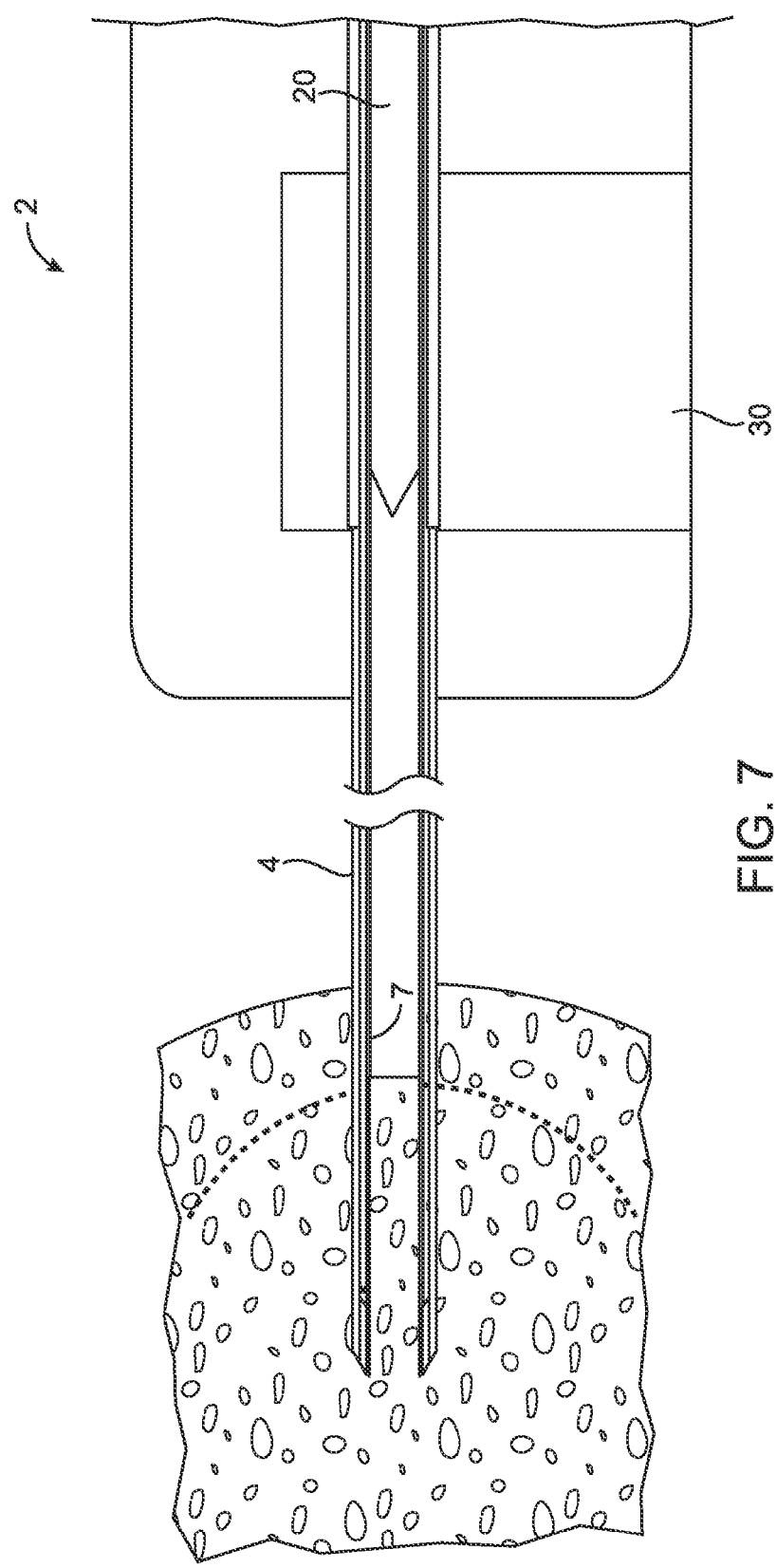
FIG. 7 shows a tubular element advanced into tissue.

The second actuator 26 is then depressed which causes the tubular element 4 to be driven forward so that tissue enters the open end 6 as shown in FIG. 7. The transport element 7 may be advanced with the tubular element 4 or may be driven independently of the tubular element 4 without departing from the invention. For example, the transport element 7 may be driven into the position of FIG. 7 after the tubular element 4 has been driven into the tissue and even after the cutting element 10 has been deployed to the position of FIG. 8. The tubular element 4 may also be rotated while being driven forward, for example, the tubular element 4 may be rotated 0.5 to 60 revolutions when driven forward. The tubular element 4 may also simply be translated (without rotating) without departing from numerous aspects of the present invention. The introducer 20 may be advanced with the tubular element 4 as shown in FIG. 7.

Figure 8:
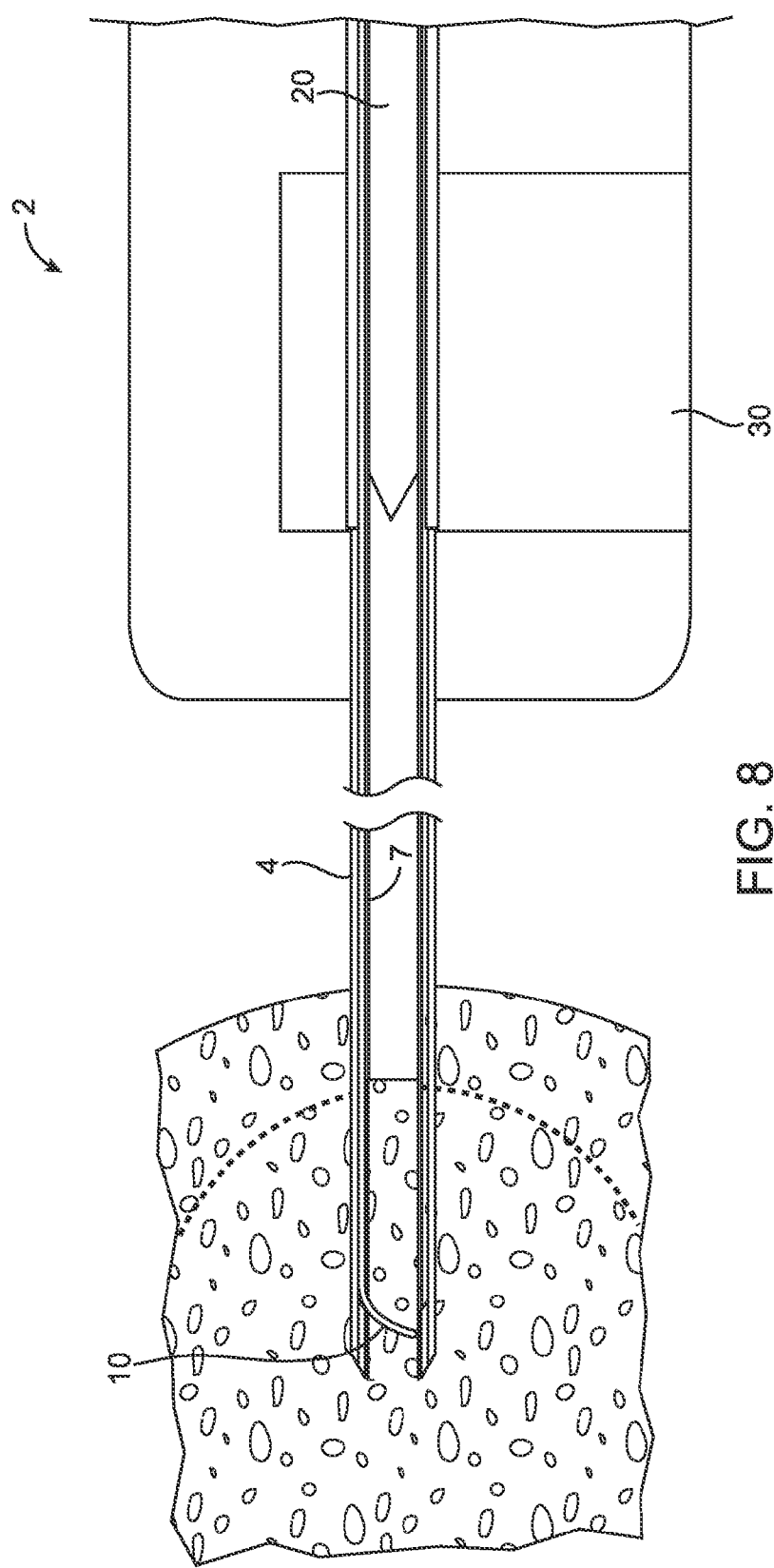
FIG. 8 shows a cutting element cutting tissue which has entered the tubular element.

The cutting element 10 is then advanced until it contacts the protrusion 11 and is directed into the tissue which has entered the tubular element 4 as shown in FIGS. 4 and 8. The cutting element 10 extends toward and through a longitudinal axis defined by the tubular element 4 and forms an angle of about 70 degrees with the longitudinal axis although any other suitable angle may be used. The cutting element 10, transport element 7 and/or tubular element 4 may also be rotated to aid in cutting the tissue. The cutting element 10 may be rotated with the tubular element 4 in the same direction or in opposite directions when parting off the tissue which has entered the device 2.

Figure 9:
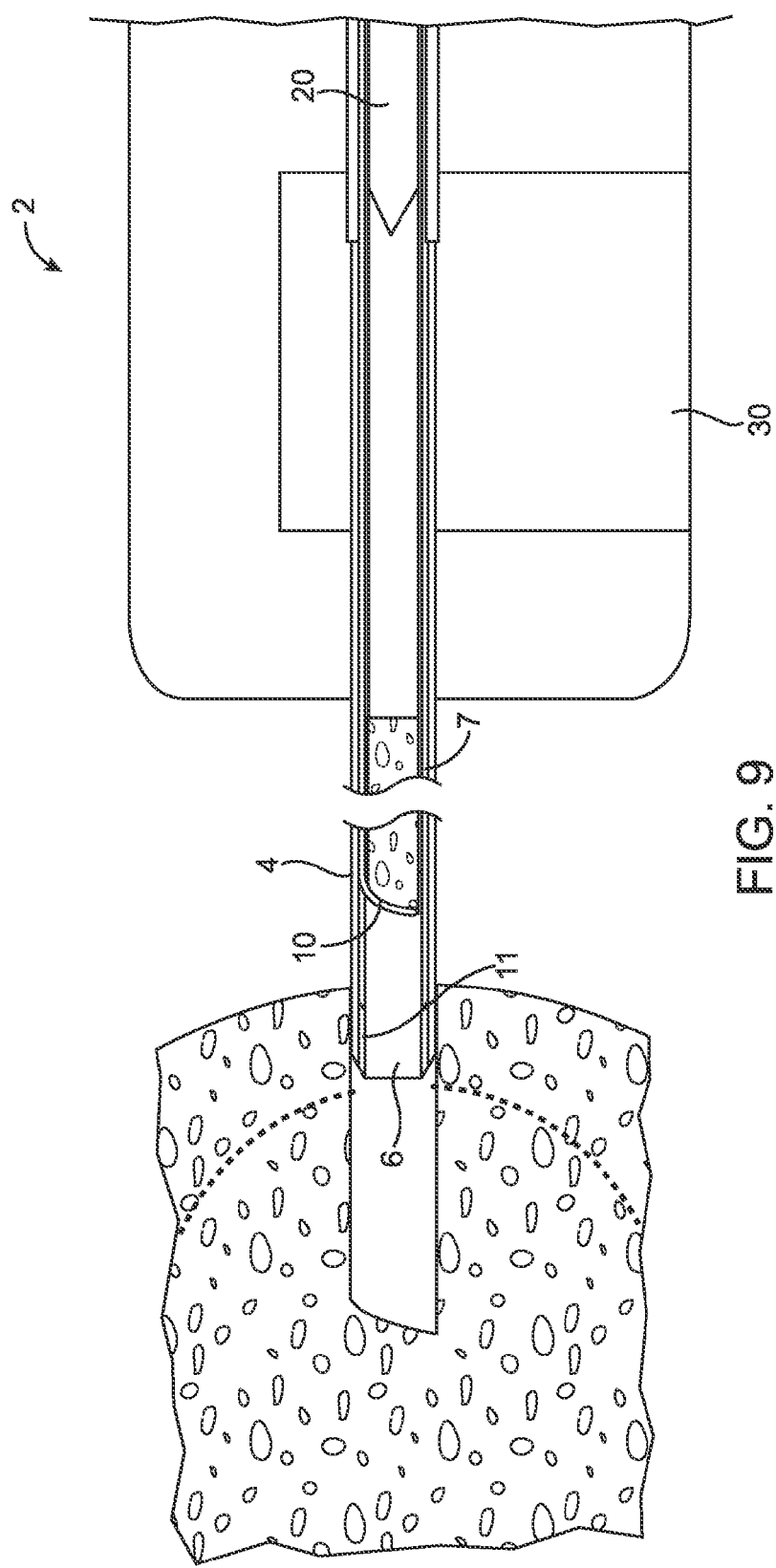
FIG. 9 shows the tissue being transported proximally.
Figure 10:
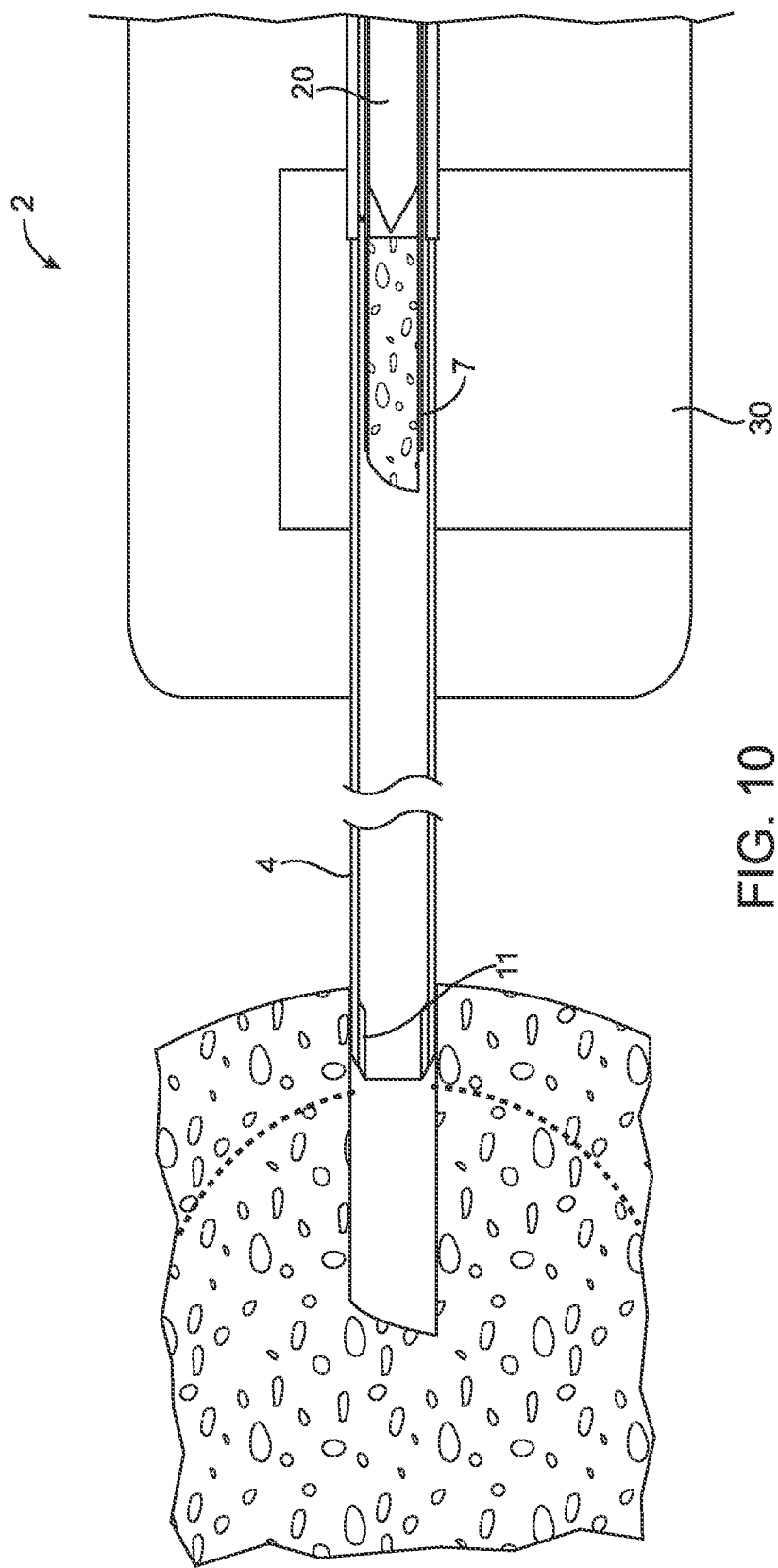
FIG. 10 shows the tissue positioned over a tissue chamber and contacting a distal end of the introducer.
Figure 11:
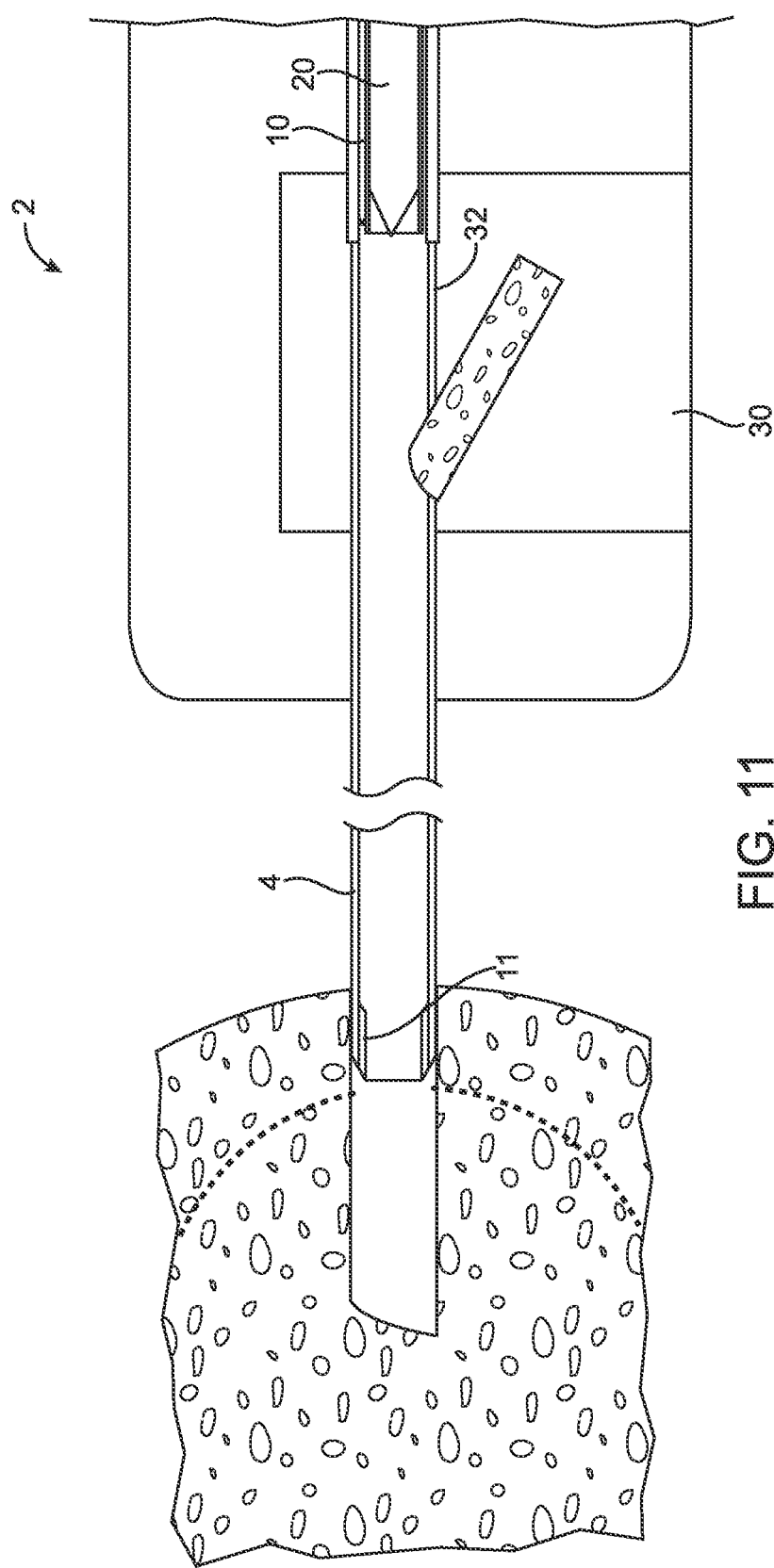
FIG. 11 shows the tissue falling into the tissue chamber.

The transport element 7 and cutting element 10 then move proximally toward the tissue chamber 30 as shown in FIG. 9. The introducer 20 is positioned so that continued proximal movement of the transport element 7 brings the tissue into contact with the distal end of the introducer 20 as shown in FIG. 10. Continued proximal movement of the transport element 7 completely exposes the tissue and permits the tissue to fall into the tissue chamber 30 as shown in FIG. 11. The tubular element 4 has an opening 32 leading to the tissue chamber 30 to permit the tissue to fall into the tissue chamber 30 when the tubular element 4 is in the position of FIG. 11.

The cutting element 10 is straightened by withdrawing the cutting element 10 into a recess (not shown). The cutting element 10 and transport element 7 are then moved back to the position of FIG. 6. The tubular element 4 may remain within the patient during transport of the tissue to the tissue chamber 30 so that the device 2 is ready to take another tissue mass without removing the device 2 from the patient. The user may re-orient the device 2 as necessary so that the tubular element 4 is directed at tissue to be removed. The user then actuates the second actuator 26 again which causes the tubular element 4 to be driven forward to collect another tissue mass. If a tissue mass is desired at another location, the user may actuate the first actuator 24 to move the introducer 20 back to the position of FIG. 5. The device 2 may then be manipulated to position the device 2 at the next location where tissue is to be removed. Of course, the introducer 20 may also be automatically repositioned after each collecting each tissue mass.

Figure 12:
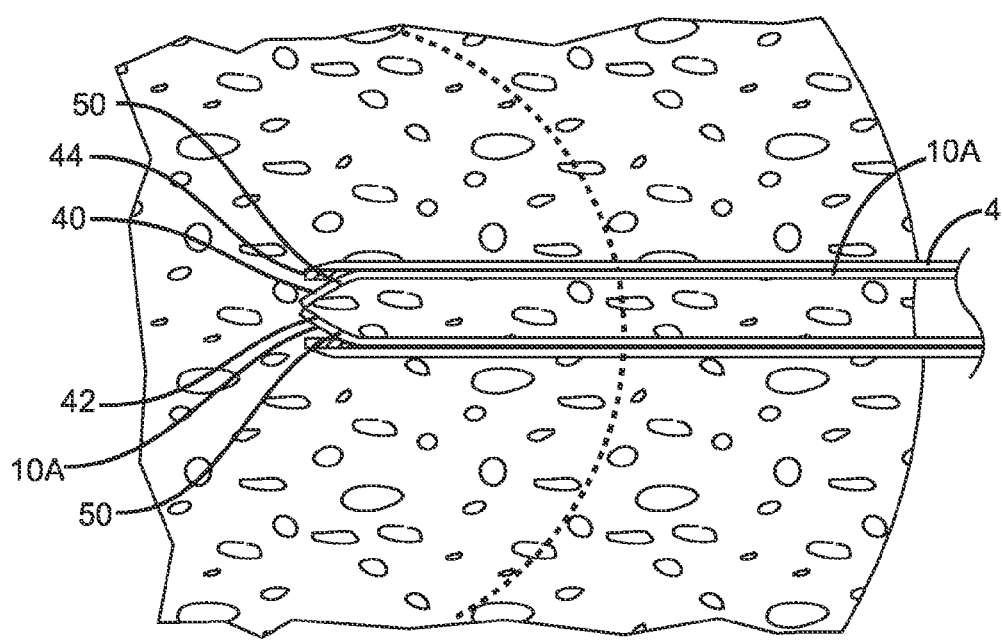
FIG. 12 is a cross-sectional view of another tissue removal device.
Figure 13:
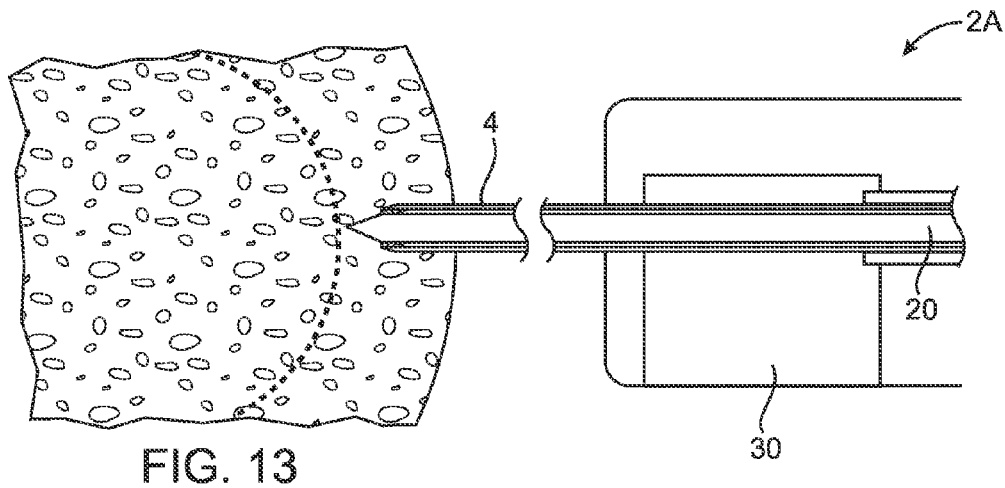
FIG. 13 shows the device of FIG. 12 introduced into tissue.

Referring to FIGS. 12-18, another device 2A for removing tissue is shown wherein the same or similar reference numbers refer to the same or similar structure. The cutting element 10A has a first part 40 and a second part 42 which may be integrally formed or may be independent elements. The first and second parts 40, 42 move inwardly to cut the tissue which has entered the tubular element 4 as shown in FIG. 12. The first and second parts 40, 42 move inwardly when they engage a protrusion 16 on an inner wall 46 of the tubular element 4A as shown in FIG. 12. The protrusion 16 may be a ring 21 which directs the first and second parts 40, 42 inwardly.

The first and second parts 40, 42 may each include a portion 50 which undergoes plastic deformation when moving to the position of FIG. 12. The first and second parts 40, 42 remain in the closed position until they are withdrawn into recesses (not shown) which straighten the two parts 40, 42. The first and second parts 40, 42 may also lock together or may be naturally biased to the position of FIG. 12 rather than being plastically deformed without departing from numerous aspects of the present invention.

Figure 17:
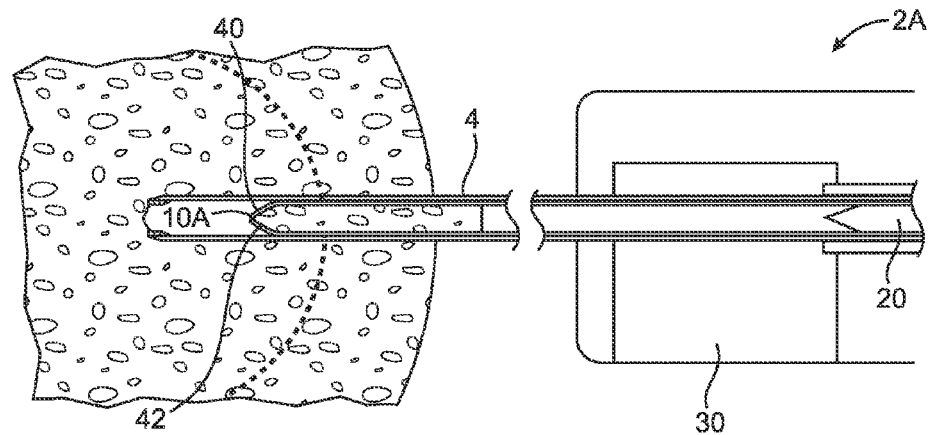
FIG. 17 shows the cutting element moving the tissue proximally toward the tissue chamber.
Figure 18:
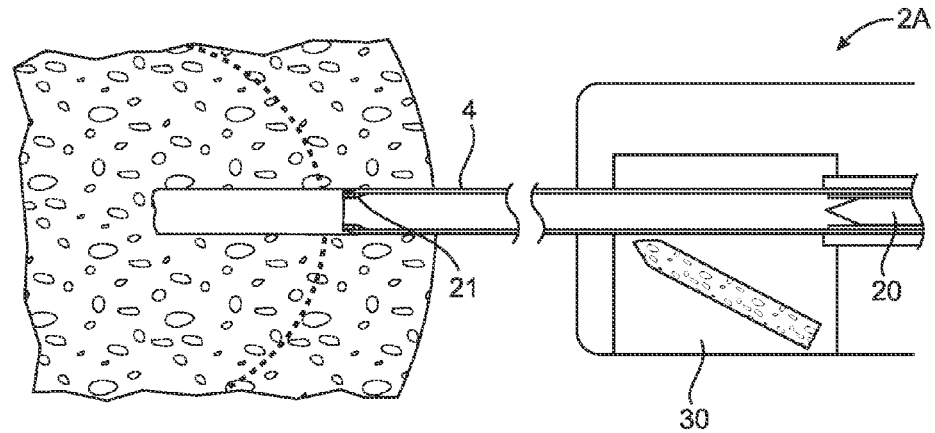
FIG. 18 shows the tissue being released into the tissue chamber by the cutting element.

The cutting element 10A is used to transport the tissue to the tissue chamber 30 after parting off the tissue. The cutting element 10A moves proximally as shown in FIGS. 17 and 18 to transport the tissue to the tissue chamber 30. The tissue may contact the introducer 20 or another part of the device 2A as the tissue is moved proximally to help release the tissue from the cutting element 10A.

Figure 14:
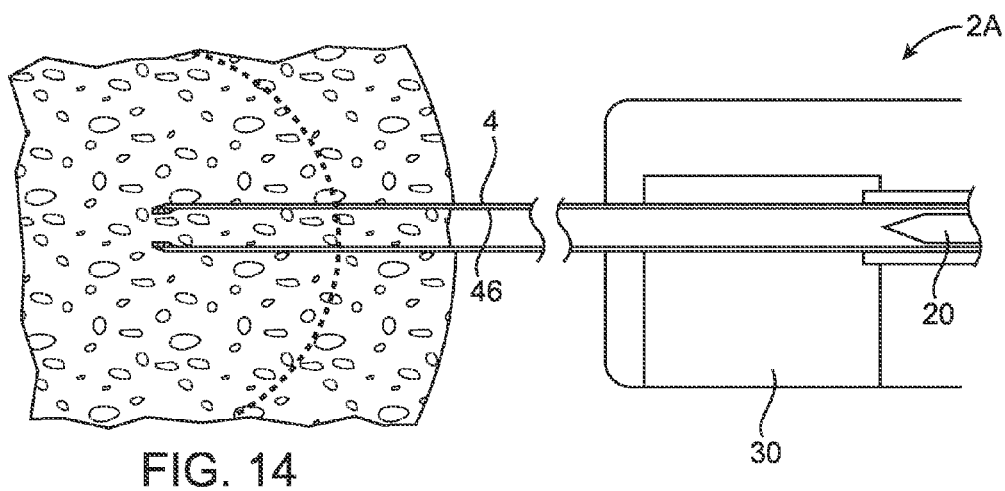
FIG. 14 shows the introducer retracted.
Figure 15:
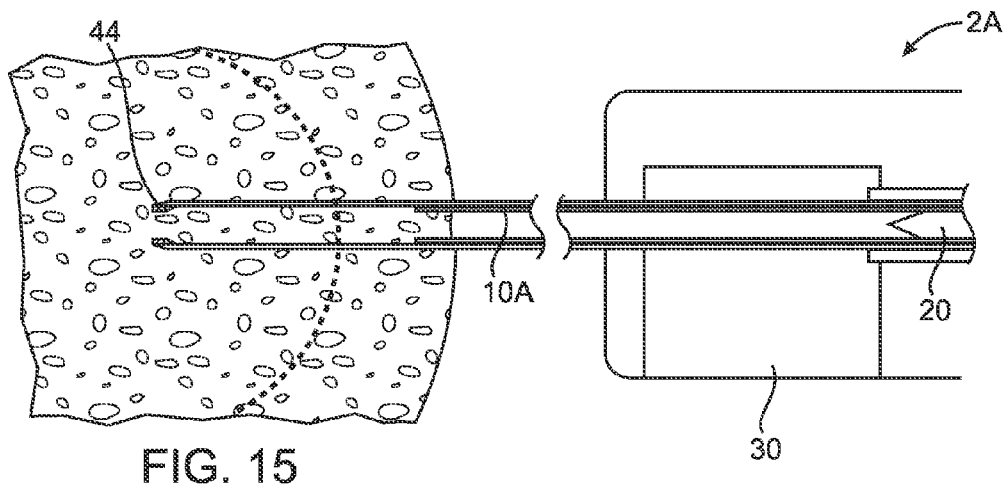
FIG. 15 shows the cutting element being advanced distally.
Figure 16:
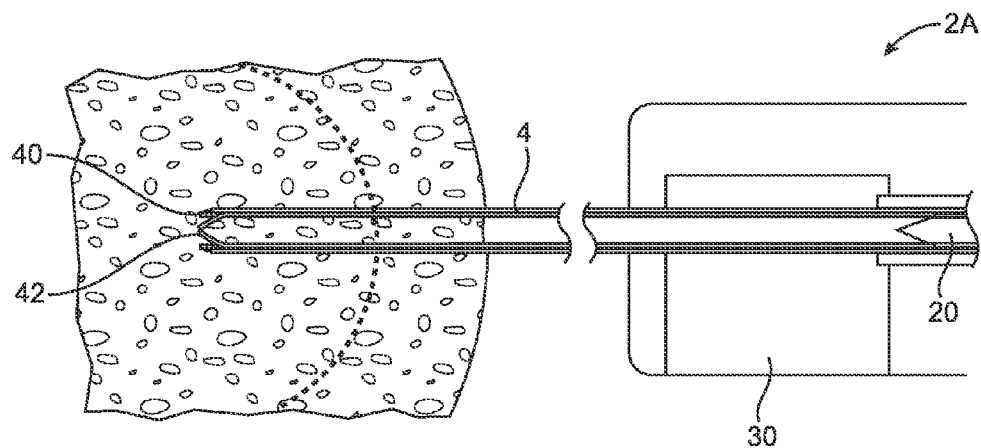
FIG. 16 shows the cutting element in a cutting position.

Use of the device 2A is similar to use of the device 2 described above. The first actuator 24 is depressed to retract the introducer 20 as shown in FIG. 14. The second actuator 26 is then depressed which causes the tubular element 4A to be advanced into tissue as shown in FIG. 14. The cutting element 10A is then advanced to part off the tissue which entered the open end as shown in FIGS. 12 and 16. The cutting element 10A may be moved together with the tubular element 4A when the tubular element 4A is advanced or may be driven over the tissue after the tissue has entered the tubular element 4A. The cutting element 10A then moves proximally toward the tissue chamber 30 as shown in FIG. 17 and deposits the tissue in the tissue chamber 30 as shown in FIG. 18. The first and second parts 40, 42 are opened when they are withdrawn into the recesses (not shown).

The tubular element 4A and cutting element 10A are then moved back into position to take another tissue mass. As such, the tissue removal device 2 does not need to be removed from the patient so that the user may simply reorient the device 2 or move the device 2 to another location where tissue is to be removed as described above. The method described in connection with FIGS. 12-18 may also be accomplished with the device of FIGS. 2-11 in that the cutting element 10 may be used to transport the tissue mass by itself. Such a method and use of the device 2 of FIGS. 1-11 is expressly incorporated here.

Figure 19:
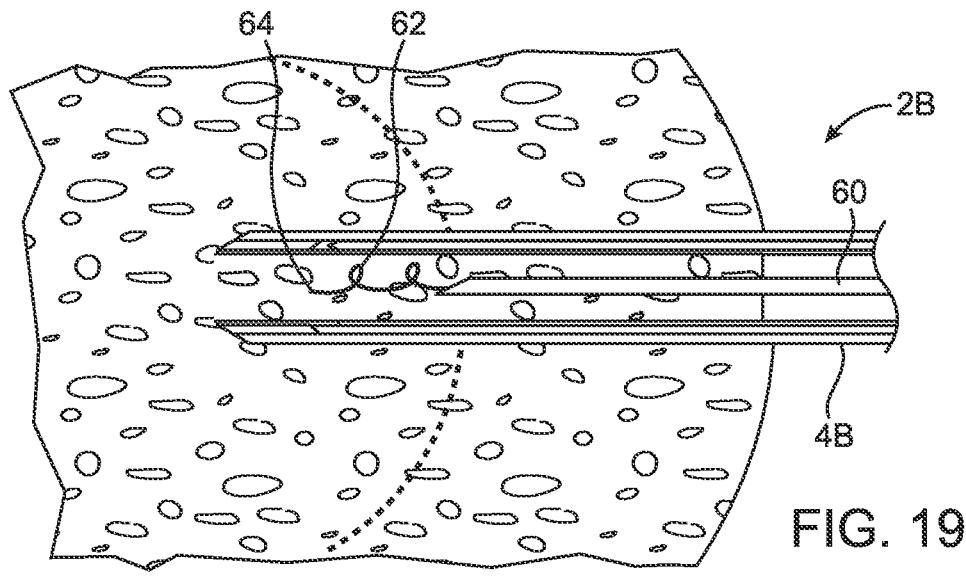
FIG. 19 shows another device for removing tissue from a patient.
Figure 20:
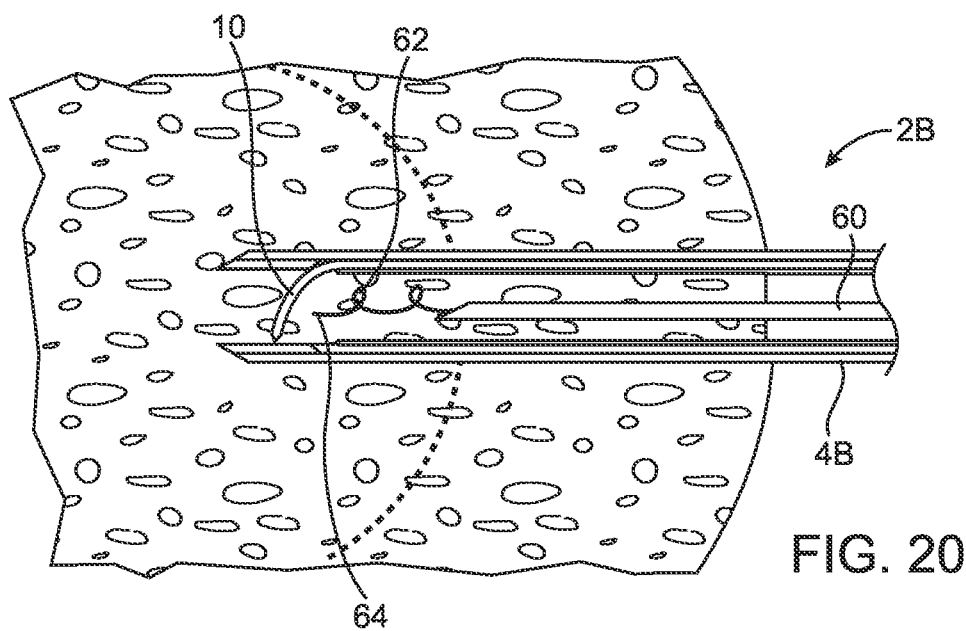
FIG. 20 shows the cutting element cutting the tissue which has entered the tubular element.

Referring to FIGS. 19 and 20, another tissue removal device 2B is shown wherein the same or similar reference numbers refer to the same or similar structure. The tissue removal device 2B has a tubular element 4B which is driven into tissue. The device 2B also has the cutting element 10 which parts off the tissue in the tubular element 4B and the tissue chamber 30 which receives the tissue (see FIGS. 1 and 2). The cutting element 10 and/or tubular element 4B may be rotated to aid in cutting the tissue. The cutting element 10 may be rotated with the tubular element 4A in the same direction or in opposite directions when parting off the tissue which has entered the device 2B. The device 2B also has the first and second actuators 24, 26 which function in the same manner as the first and second actuators 24, 26 described above (also shown in FIGS. 1 and 2).

The device 2B also includes a transport element 60 which moves within the tubular element 4B and engages the tissue. The transport element 60 may be any suitable element which engages and contacts the tissue mass. For example, the transport element 60 may be a wire 62 having a sharp tip 64 which pierces the tissue. The wire 62 may be curved or helical so that the wire 62 may be pivoted or rotated into engagement with the tissue. The transport element 60 may be advanced into the tissue before the tubular element 4B or may be driven into the tissue at the same time as the tubular element 4A or even after the tubular element 4B has been driven into the tissue.

Once the transport element 60 and the tubular element 4A are in the position of FIG. 20, the transport element 60 moves proximally to carry the tissue toward the tissue chamber 30. The transport element 60 may also be rotated in the same direction that was used to engage the tissue when transporting the tissue mass proximally to help maintain engagement with the tissue. The tissue is transported proximally until the tissue contacts the introducer 20 in the manner described above (see FIG. 11). The transport element 60 is then withdrawn thereby permitting the tissue mass to fall into the chamber 30. The transport element 60 may be rotated when being withdrawn from the tissue so that the wire 62 withdraws smoothly from the tissue. The transport element 60, tubular element 4A and cutting element 10 are then moved back into position to take another tissue mass without removing the device 2B from the patient as described above.

Figure 21:
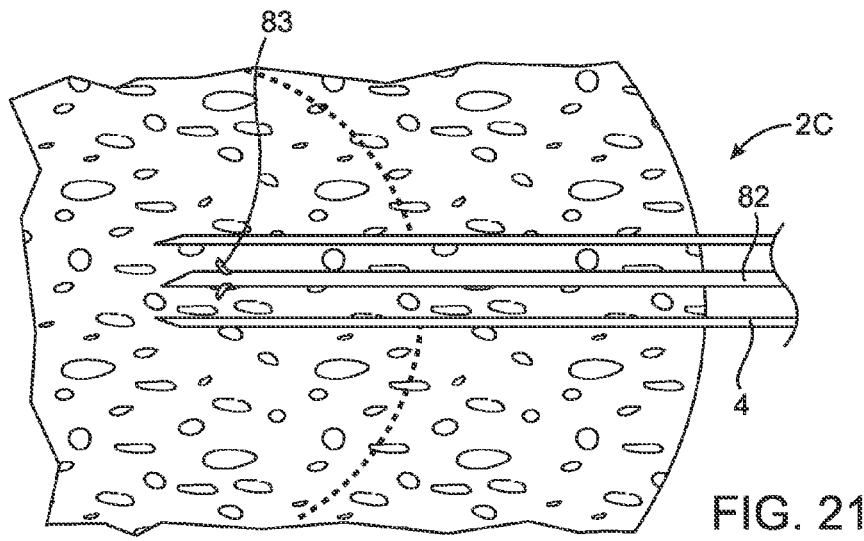
FIG. 21 shows still another device for removing tissue from a patient.
Figure 22:
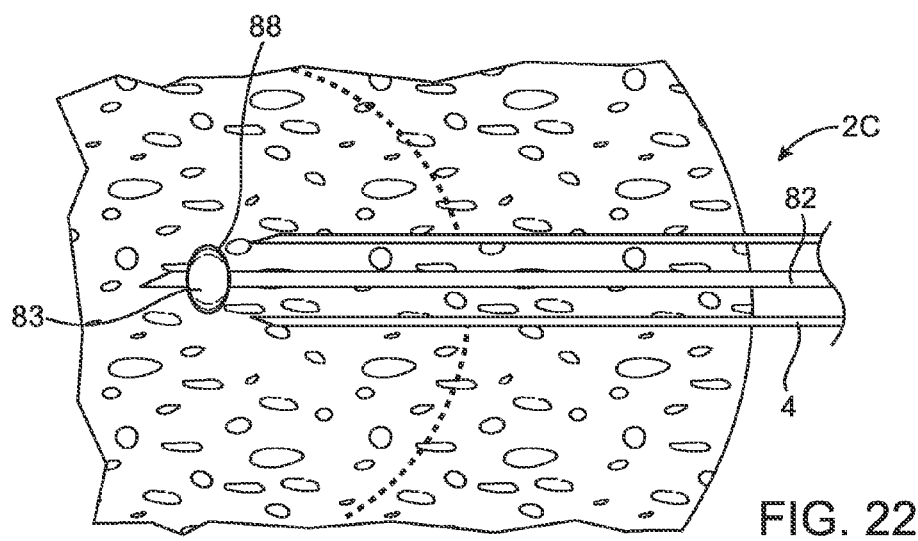
FIG. 22 shows another anchor for the device of FIG. 21.
Figure 23:
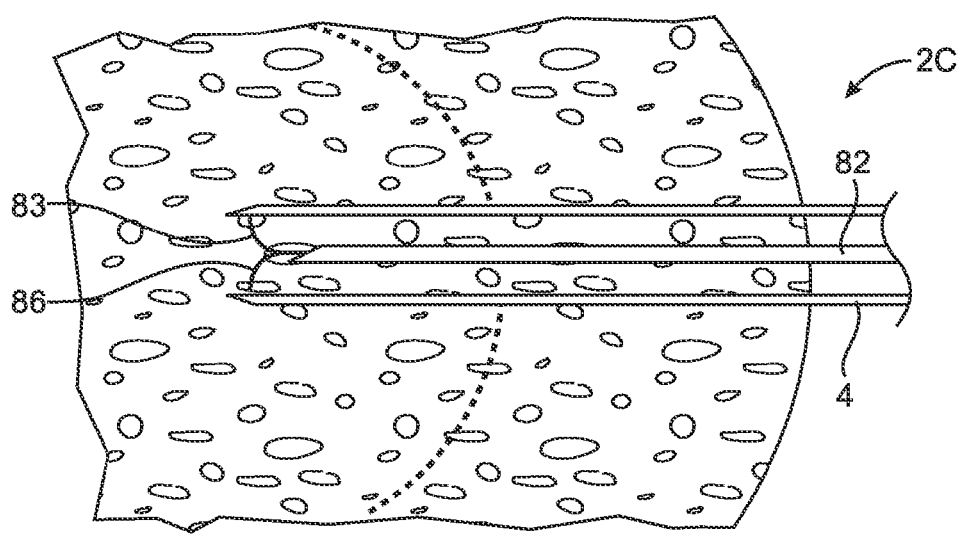
FIG. 23 shows still another anchor for the device of FIG. 21.

Referring to FIG. 21, another tissue removal device 2C is shown wherein the same or similar reference numbers refer to the same or similar structure. The device 2C has a piercing element 82 which pierces the tissue. The piercing element 82 also has a deployable anchor 83 which secures the tissue to the piercing element 82. The anchor 83 may take any suitable form. For example, the anchor 83 may be one or more retractable barbs 84 which hold the tissue as shown in FIG. 21. The barbs 84 may be slightly curved to help hold the tissue on the piercing element 80 but may take any other suitable shape. The anchor 82 may also be one or more wires 86 extending from the piercing element 82 as shown in FIG. 22 or may be an inflatable balloon 88 as shown in FIG. 23.

The device 2C also has the first and second actuators 24, 26 (see FIGS. 1 and 2) which operate in the manner described above. The device also has a third actuator 27 which advances the piercing element 82 when actuated. The piercing element 82 is then moved proximally after the third actuator 27 is actuated again as described below to transport the tissue to the tissue chamber 30.

The device 2C may be operated in a number of different ways including the two now described. In one method, the piercing element 82 is driven into the tissue before the tubular element 4 when the user actuates the third actuator 27. The tubular element 4 is then driven over the piercing element 82 when the user actuates the second actuator 26. The piercing element 82 is then moved proximally to tear the tissue from the surrounding tissue. This step may be performed manually or by actuating the third actuator 27 again. The tissue is then transported proximally by actuating the third actuator 27 again if the user has parted-off the tissue manually.

The piercing element 82 moves proximally until the tissue is over the tissue chamber 30 at which time the anchor 83 is automatically released by withdrawing the barbs 84 or wires 86 or deflating the balloon 88. Further retraction of the piercing element 80 withdraws the piercing element 80 completely thereby permitting the tissue to fall into the tissue chamber 30 as described above in connection with the other devices 2, 2A, 2B. After the tissue has been deposited into the tissue chamber 30, the device 2C is ready to take another sample without removal from the patient as described above.

In another method of operating the device 2C, the tubular element 4 is driven into the tissue first and the piercing element 82 is then driven into the tissue after the tissue has entered the tubular element 4. The anchor 83 is then deployed to secure the tissue to the piercing element 80. The tissue is then separated from the surrounding tissue and transported to the tissue chamber 30 as described above.

Figure 24:
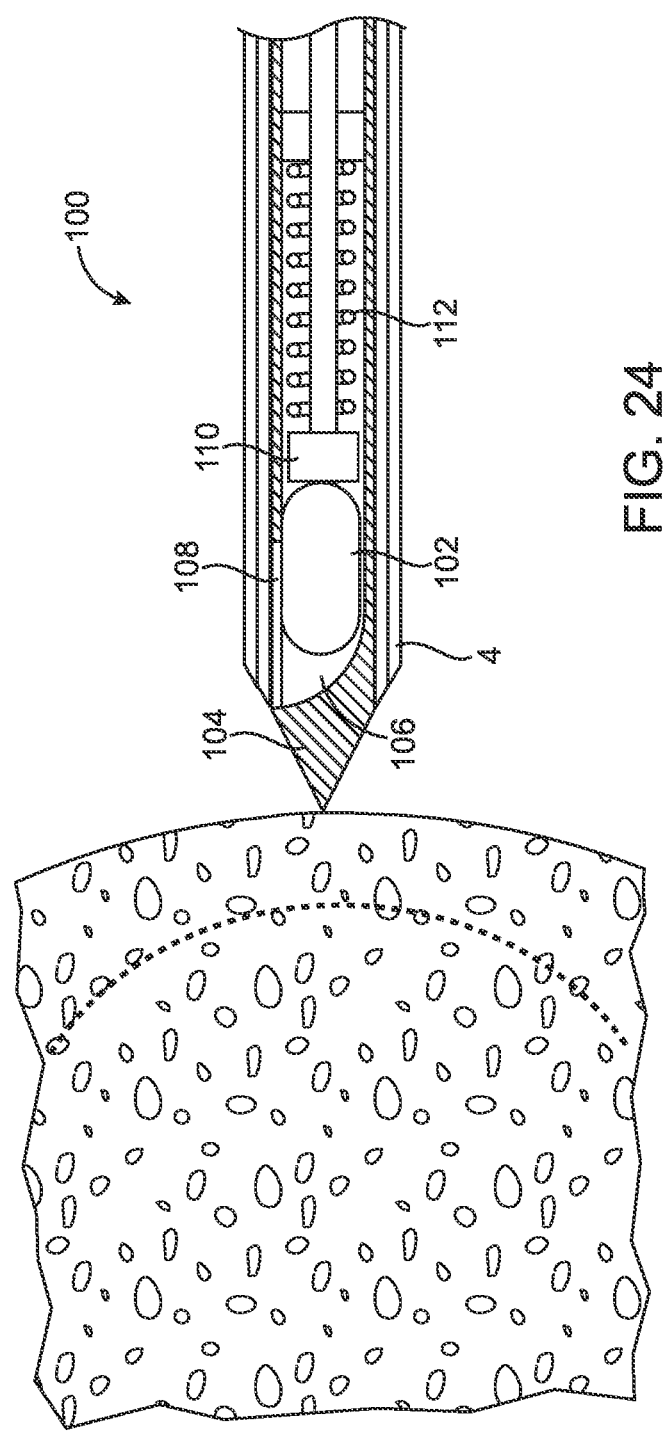
FIG. 24 is a cross-sectional view of another device for removing tissue from a patient and placing a marker in the patient.
Figure 25:
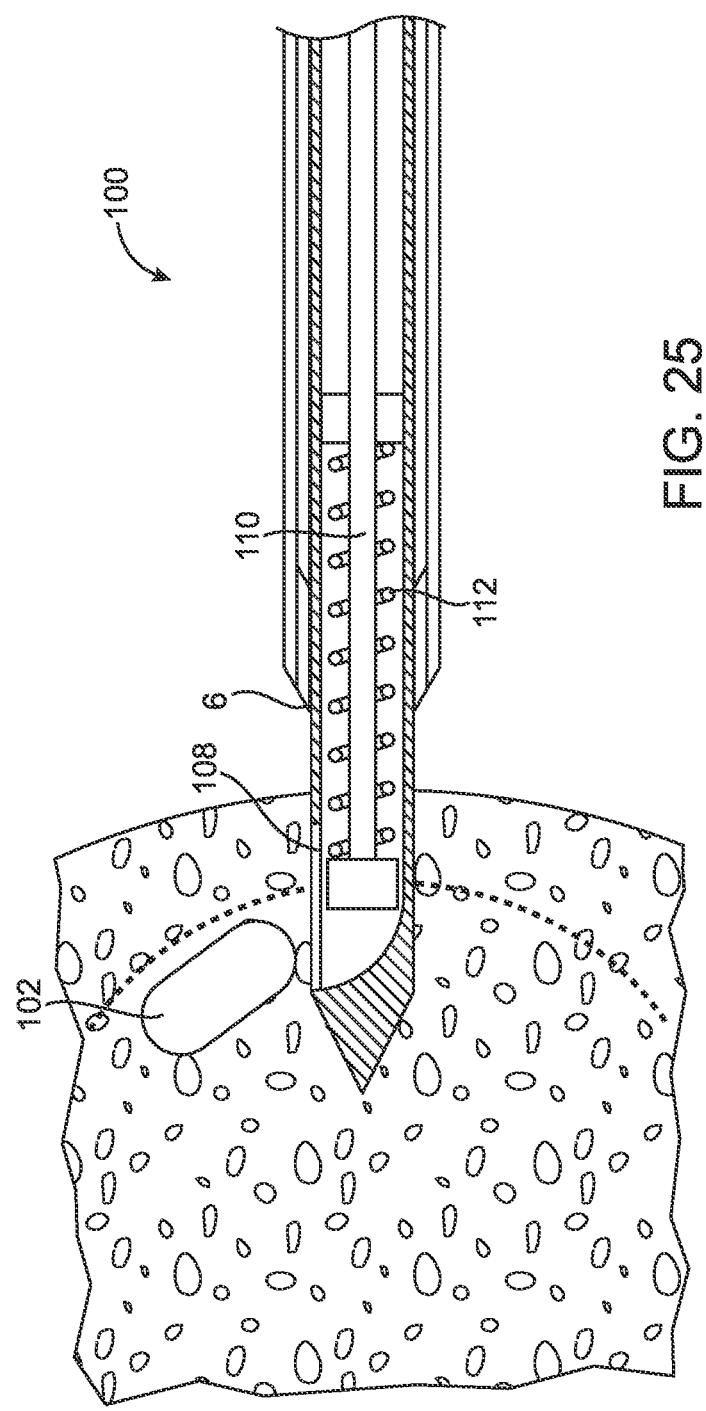
FIG. 25 shows the introducer moved to a position which releases the marker.

Referring to FIGS. 24 and 25, another tissue removing device 100 is shown. The device 100 may also be used to remove tissue and to place a marker 102 in the patient. The device 100 is similar to other devices described herein, such as the device 2A of FIGS. 16-18, and the same or similar reference numbers refer to the same or similar structure. The device 100 may include the same features and may be used in substantially the same manner as the device of FIGS. 16-18 and all disclosure related to the structure and use of device 2A is incorporated here. The marker 102 may be any suitable marker such as a polylactic-polyglycolic acid copolymer with a metallic clip or a collagen material with a metallic clip contained therein and may be used for any purpose such as marking a breast. The marker 102 is preferably a solid marker rather than a dye or liquid. The term "solid" as used herein may include soft materials such as gel-like materials or otherwise flexible materials so long as the material is not a liquid which may disperse and/or reduce in concentration over time.

The marker 102 may be delivered at a time selected by the user as described herein. The marker 102 is mounted to an introducer 104 which has a sharp distal end 106 to pierce tissue when introducing the device 100. Of course, the device 100 may also be introduced through a trocar, sheath, cannula or the like as described above. The marker 102 is stored within a recess 106 in the introducer 104. The introducer 104 also has a port 108 through which the marker 100 leaves the introducer 104. A pusher 110 moves the marker 102 out of the port 108 when the port 108 is exposed as shown in FIG. 25. The pusher 110 is biased by a spring 112 to automatically move the marker 102 out of the port 108 when the port 108 is exposed. The marker 102 may also be moved out of the opening by using a pulse of fluid (either a gas such as carbon dioxide or a liquid such as saline) to exert pressure on the marker 102 to force the marker out of the opening.

Use of the device 100 is now described. The device 100 may be used to remove a number of tissue masses from a patient in the same manner as described above. The device 100 may include the cutting element 10A (see FIGS. 16-18) or any other suitable structure or method may be used to cut, part-off or otherwise separate the tissue in the device 100 from the surrounding tissue including any of those described herein. Furthermore, the device 100 is shown having the open distal end 6 but may have a side opening rather the opening 6 at the distal end without departing from various aspects of the invention. When the user desires to place the marker 102 in the patient, an actuator is actuated which causes the introducer 104 to be advanced to the position of FIG. 24 which is essentially the same position used when introducing the device 100 into the patient. The introducer 104 may then continue to move distally thereby exposing the port 108. Alternatively, the tubular element 4 may be withdrawn to expose the port 108 or the port 108 may be exposed by a combination of advancing the introducer 104 and withdrawing the tubular element 4.

Figure 26:
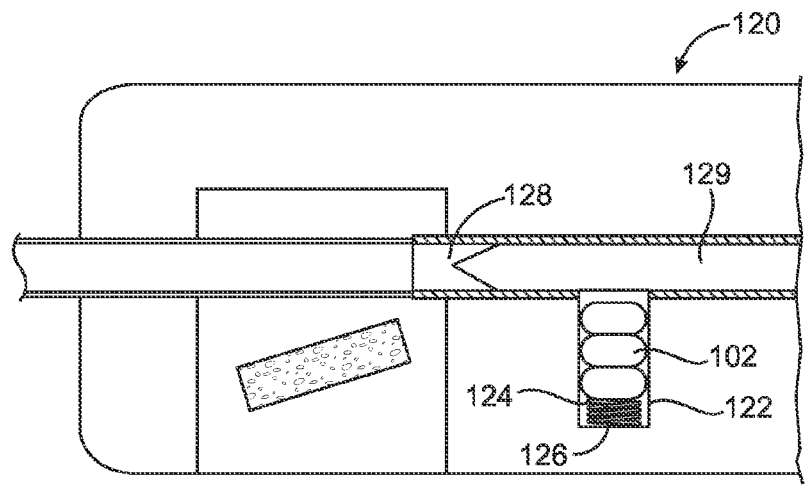
FIG. 26 shows still another device for removing tissue from a patient and placing a marker in the patient with the introducer withdrawn to permit tissue to be collected
Figure 27:
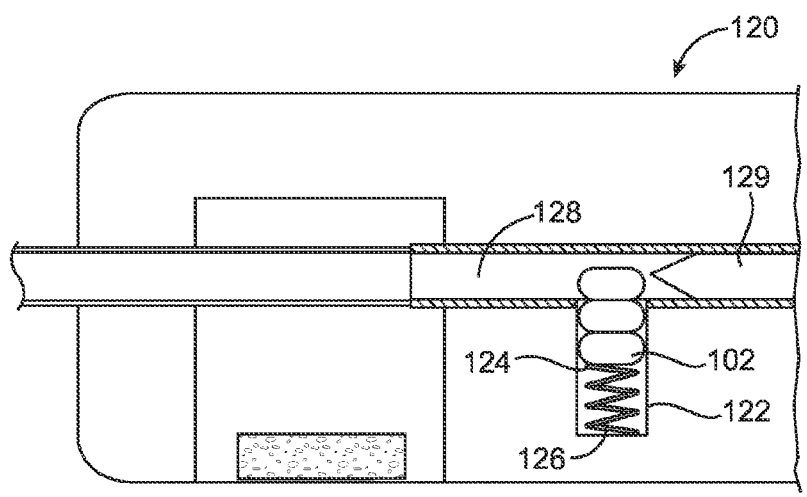
FIG. 27 shows the introducer withdrawn proximal to a marker storage area.
Figure 28:
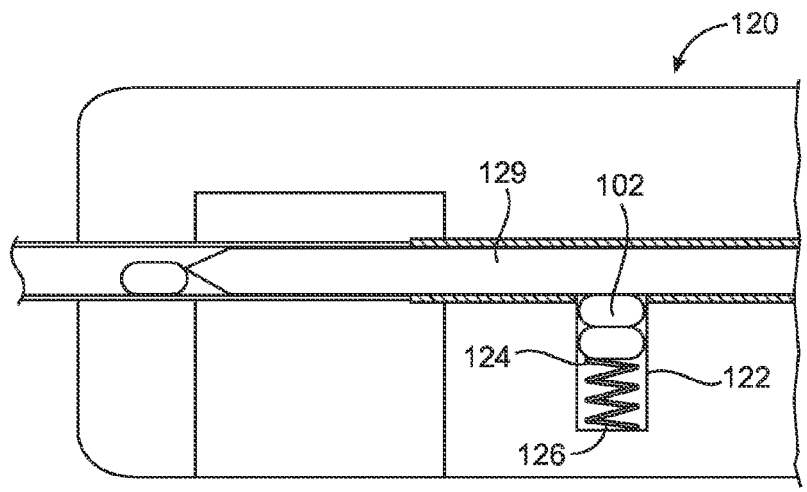
FIG. 28 shows the introducer advancing the marker toward the open end.

Referring to FIGS. 26-28, another device 120 is shown which may be used to remove tissue from a patient and also place the marker 102 in the patient. The device 120 is also similar to the device 2A of FIGS. 16-18 and discussion of the device 2A and methods of use are expressly incorporated here. FIGS. 26-28 show a proximal part of the device 120 to illustrate storage and delivery of the marker 102. The marker 102 is contained in a storage area 122 in the device 120. The device 120 stores three markers 102 although any suitable number may be stored. The marker storage area 122 also has a pusher element 124 which is biased by a spring 126 to move the marker out of the area 122 and into a lumen 128. The device 120 also has an introducer 129 which is withdrawn to the position of FIG. 27 so that one of the markers 102 may move into the lumen 128. The marker 102 is then moved through the lumen 128 and ultimately out of the distal opening by the introducer 129 as shown in FIG. 28. The device 120 also includes an actuator (not shown) which is actuated by the user when the user desires to implant the marker 102. Upon actuation, the introducer 129 is automatically withdrawn to the position of FIG. 27 to permit one of the markers 102 to enter the lumen 128. The introducer 129 then automatically moves distally to push the maker 102 out through the open end 6 of the tubular element 4.

Use of the device 120 is now described. The device 120 may be used to remove a number of tissue masses from a patient as described above. Although the device 120 is shown with the cutting element 10A, any other suitable structure or method may be used to cut, part-off or otherwise separate the tissue in the device 120 from the surrounding tissue such as those described herein. When the user desires to place the marker 102 in the patient, the suitable actuator 24, 26, 27 is actuated. The introducer 129 is then retracted proximal to the marker storage area 122 as shown in FIG. 27. One of the markers 102 is then moved into the lumen 128 by the pusher 124. The introducer 129 is then automatically advanced so that the marker 102 is pushed out through the open end 6 of the device 120 as shown in FIG. 30.

Figure 29:
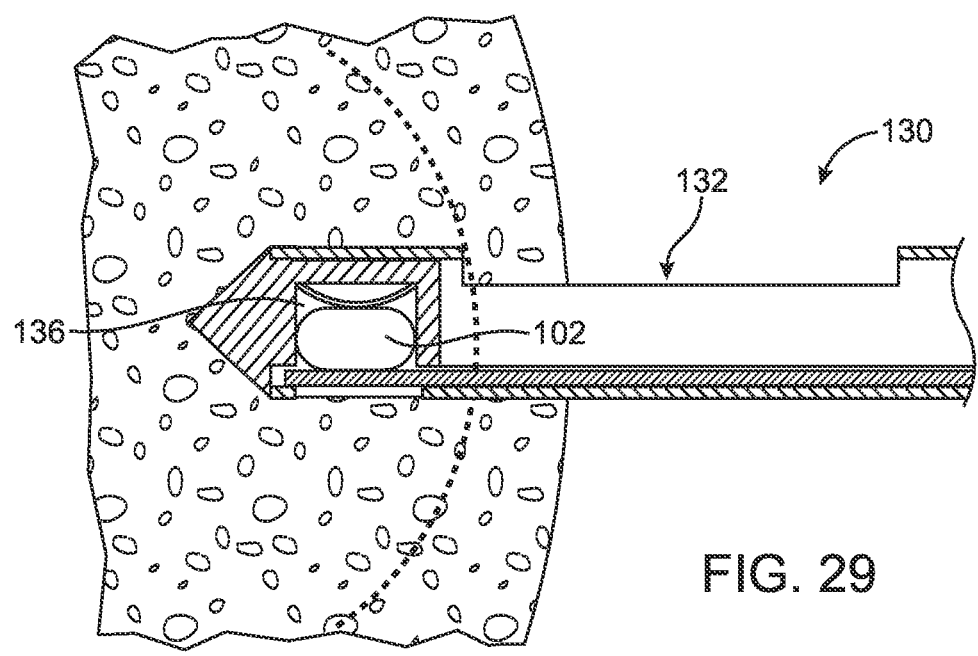
FIG. 29 shows yet another device for removing tissue from a patient and placing a marker in the patient with a cutting element cut tissue which has entered the device through a side opening.
Figure 30:
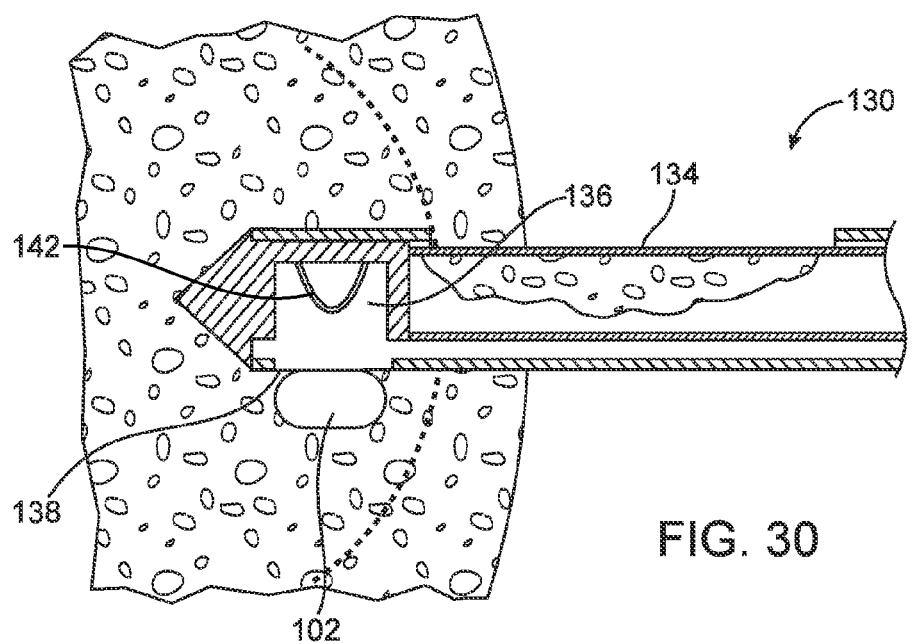
FIG. 30 shows the marker being released from a marker storage area.

Referring now to FIGS. 29 and 30, yet another device 130 for removing tissue and placing the marker 102 within a patient is shown. The device 130 has a side opening 132 through which tissue enters the device 130. A cutting element 134 shears off material which extends into the device 130 through the opening 132 as shown in FIG. 28. The device 130 may use suction to draw tissue into the opening 132 or may be forced laterally so that tissue enters the opening 132. The device 130 also includes the marker 102 housed in a marker storage area 136 positioned distal to the side opening 132. The marker storage area 136 has an opening 138 which is covered with a sliding door 140. When the door 140 is opened as shown in FIG. 29, a spring-loaded pusher 142 forces the marker 102 out of the opening 138. The marker 102 is released at the desired time by the user upon actuation of an actuator (see actuators 24, 26, 27 of FIG. 1). The marker 102 may also be delivered through the opening 132 through which tissue is removed without departing from various aspects of the invention.

Referring to FIGS. 31-34, still another device 200 for removing tissue and marking a tissue area is shown wherein the same or similar reference numbers refer to the same or similar structure. The device 200 is similar to the devices described above and the features and use of the devices described above are incorporated here. The device 200 has a tissue marking element 202 which delivers a flowable substance 204 to mark tissue in the patient. The flowable substance 204 may be any suitable substance which may visualized after the procedure using a suitable technique such as x-ray or ultrasound.

Figure 34:
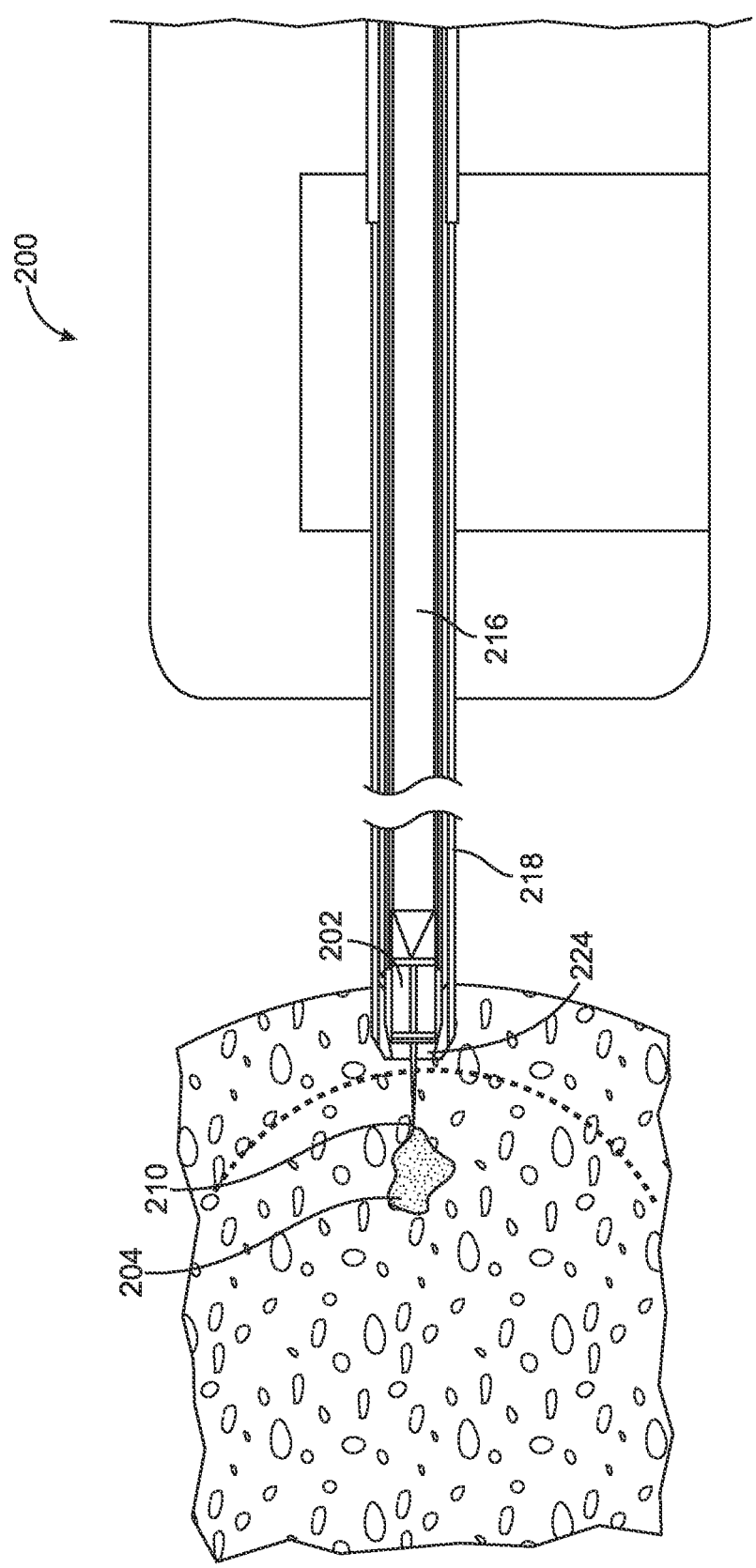
FIG. 34 shows the introducer advanced to move a piston within the tissue marking element to force the flowable substance into the tissue area.

The tissue marking element 202 has a chamber 206 which holds the flowable substance 204. The tissue marking element may also include a needle 208 having an outlet 210 through which the substance 204 is delivered. A piston or plunger 212 forces the flowable substance 204 through the outlet 210 as shown in FIG. 34.

The device 200 may be used to remove tissue using any suitable method including all of those described herein which are expressly incorporated here. The flowable substance 204 may be applied when the user desires upon actuation of the appropriate actuator (see actuators 24, 26, 27 of FIG. 1). For example, the user may first remove a number of tissue masses as described herein followed by delivery of the flowable substance 204 to mark tissue. Alternatively, the flowable substance 204 may be automatically delivered after a set or predetermined number of tissue masses have been removed.

Figure 31:
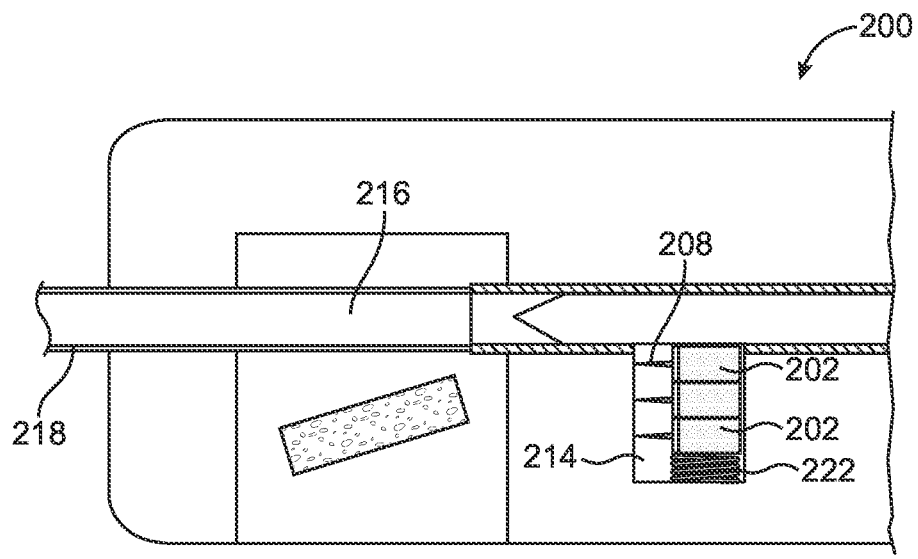
FIG. 31 shows another device for removing tissue and marking a tissue area.
Figure 32:
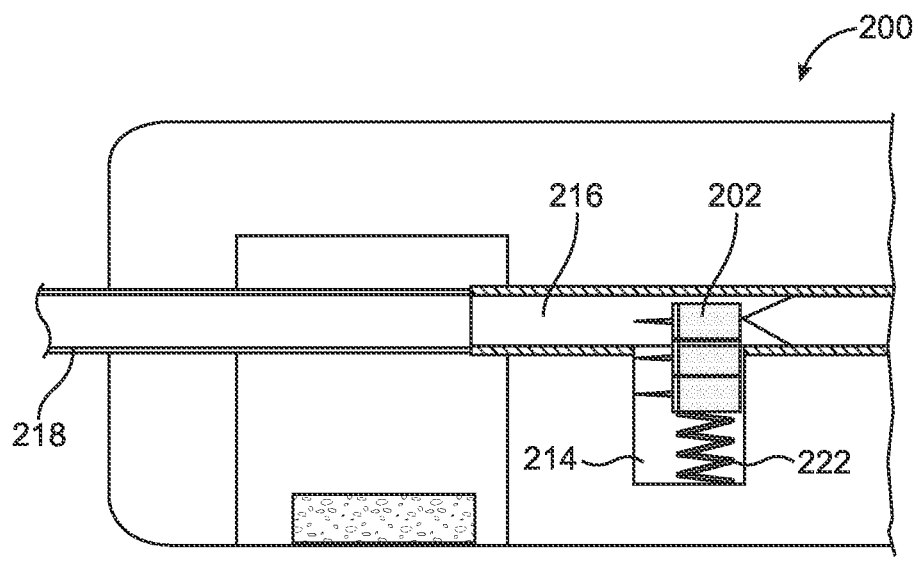
FIG. 32 shows a tissue marking element entering the lumen.
Figure 33:
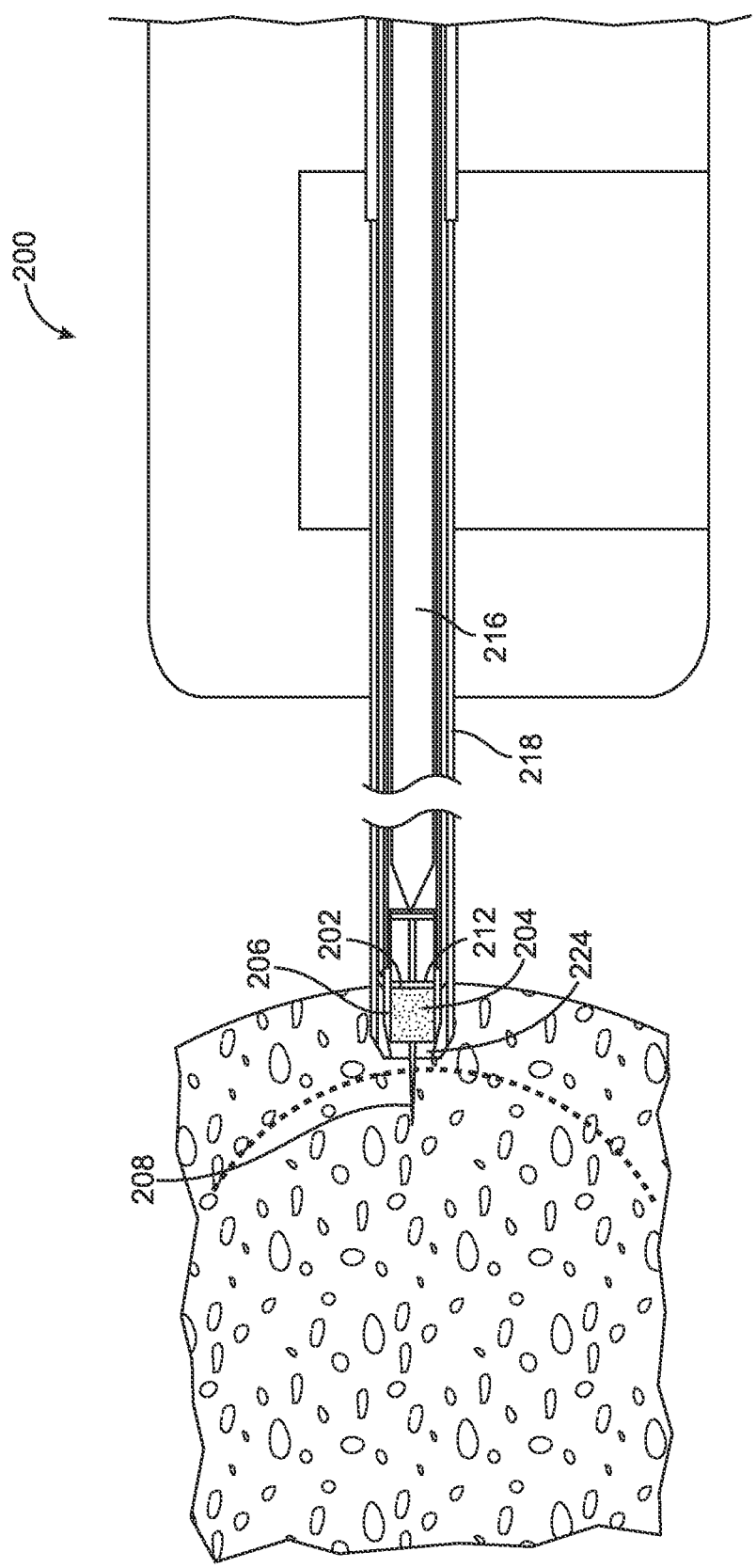
FIG. 33 shows the tissue marking element advanced to the distal end of the lumen with the introducer.

The tissue marking element 202 is stored in a marker storage area 214 adjacent to a lumen 216 in a tubular element 218 similar to other embodiments described herein as shown in FIG. 31. The device may include a storage area for a number of tissue marking elements 202 and FIG. 31 shows three tissue marking elements 202 in the storage area 214. An introducer 220 is retracted to the position of FIG. 32 which permits the tissue marking element 202 to enter the lumen 216. A spring 222 may be used to force the tissue marking element 202 into the lumen 216. The tissue marking element 202 is then advanced through the lumen 216 by the introducer 220 until the needle 208 pierces the tissue as shown in FIG. 33. The tissue marking element 202 and lumen 216 are configured so that the tissue marking element 202 cannot pass completely through an opening 224 at the distal end of the lumen 216. Once the tissue marking element 202 is positioned at the opening 224 as shown in FIG. 32 further distal movement of the introducer pushes the plunger 212 so that the flowable substance is delivered through the outlet and into the tissue as shown in FIG. 34.

Referring to FIGS. 35 and 36, still another device 300 for removing tissue and marking a tissue site is shown wherein the same or similar reference numbers refer to the same or similar structure. The device 300 is similar to the devices described above and all features and methods of use described herein are incorporated here. The device 300 includes an introducer 302 which has container 303 which holds the flowable substance 307. The container 303 may simply be a lumen 304 having one or more outlets 306 formed at the distal end of the introducer 302 through which the flowable substance 307 is delivered. A piston 308 is movable within the lumen 304 to force the flowable substance 307 through the outlets 306. The outlets 306 may be formed by elastomeric portions 310 in a manner similar to a one-way valve, such as a duckbill valve, so that the outlets 306 are normally closed to prevent the flowable material 307 from escaping. The outlets 306 will also inhibit material from entering the lumen 304. The lumen 304 may have one outlet 306 or a plurality of outlets 306 configured in a recognizable pattern which may be useful to orient or otherwise help identify the position and/or orientation of the tissue area of interest when viewed at a later time. For example, the outlets 306 may be configured in a triangle or any other suitable shape.

Referring to FIGS. 37 and 38, yet another device 400 for removing a tissue mass and marking a tissue area is shown. The device 400 is similar to the devices described above and all common features and methods described above are incorporated here. The device includes an introducer 402 having a lumen 404 in which a tissue marking element 406 is positioned. The tissue marking element 406 has a plunger 408 which is depressed by a pusher element 411 to force the flowable substance through an outlet 412 in the tissue marking element 406. A spring 414 holds the tissue marking element 406 in the stored position of FIG. 37. The tissue marking element 406 may also include a needle 416 having the 412 which deposits the flowable substance into tissue when the needle 416 pierces tissue.

Figure 39:
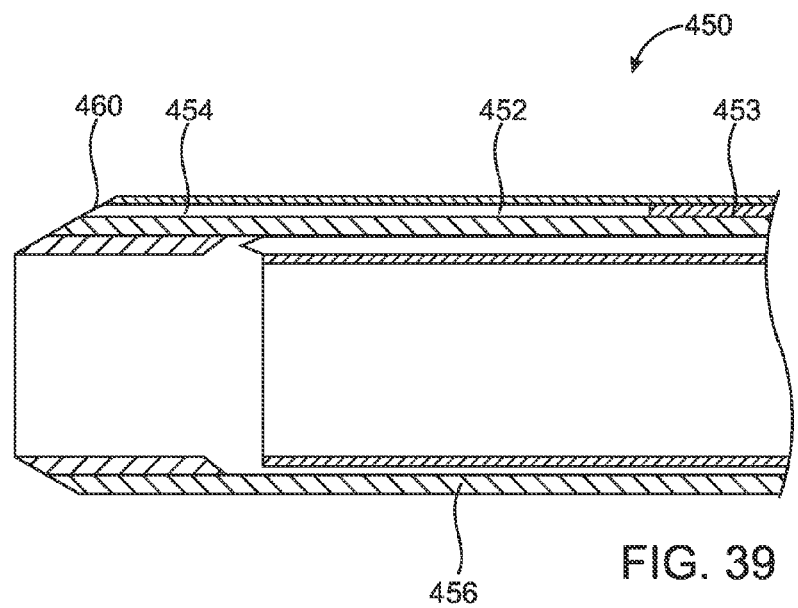
FIG. 39 shows yet another device for removing tissue and marking a tissue area.
Figure 40:
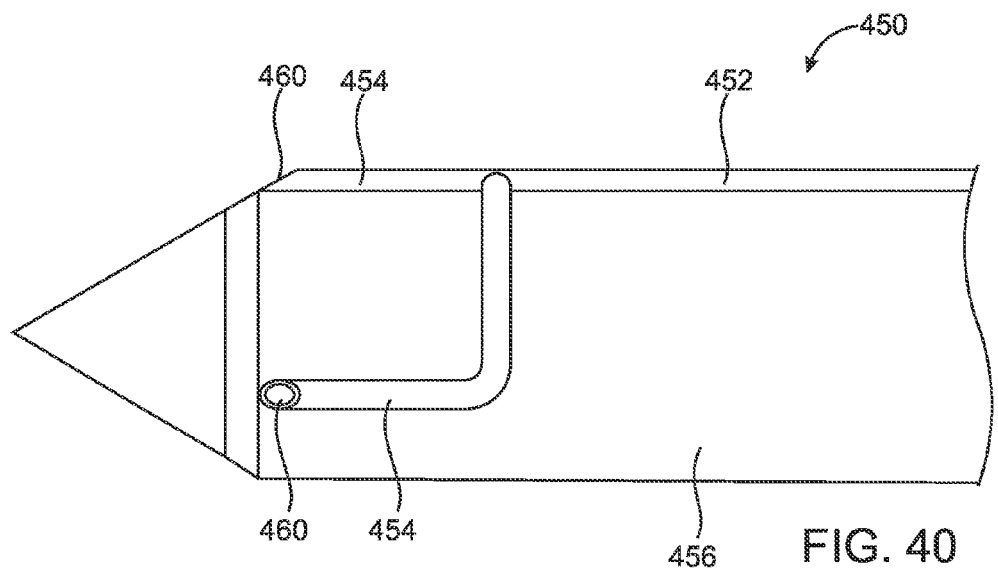
FIG. 40 shows an external view of the device of FIG. 39.

Referring now to FIGS. 39 and 40, still another device 450 for removing tissue and marking a tissue area is shown. The device 450 is similar to other devices described herein and all such uses and features of those devices are incorporated here. For example, the device 450 may be used to remove and collect tissue in any manner described herein prior to marking of the tissue area.

The device 450 has a chamber or container 452 which holds the flowable substance 307. The container 452, which may simply be a length of tubing, is coupled to a lumen 454 through which the flowable substance 307 may be delivered. The container 452 and lumen 454 are coupled to a tubular element 456 but may also be integrated into the tubular element 456. The lumen 454 has an outlet 460 through which the flowable substance 307 is delivered. The container 452 may be coupled to a series of lumens 454 each having one or more outlets 460. For example, the device may have three outlets positioned 120 degrees apart to form a recognizable pattern. The pattern may be used to orient and/or identify the tissue area which has been marked when viewed using ultrasound, x-ray or another suitable visualization technique at a later time. The outlets 460 are positioned on an outer surface of the tubular element 456 near a distal end of the tubular element 456. Of course, the device 450 may include any number of outlets 460 including only one outlet 460. The outlets 460 may also be normally closed similar to a one-way valve as described in connection with the outlets 306 of FIGS. 35 and 36. A plunger 453 is used to force the flowable substance 307 through the outlets 460.

The tissue removing devices described in FIGS. 31-40 may be used to collect a number of tissue masses in any suitable manner described herein and all such uses are incorporated here in combination with the structure and features associated with marking tissue.

Referring now to FIGS. 41-50, another device 500 having a body 501 for removing tissue is now described. The tissue removal device 500 includes a tubular element 502 having an open end 504 which is driven into tissue, with or without rotation, in any manner described herein. A cutting element 506 has a number of cutting parts 508 which are deformed, and optionally plastically deformed, to part off tissue similar to other embodiments described herein. The cutting parts 508 are deformed by a shoulder 509 on the tubular element 502 which deflects and deforms the cutting parts 508 radially inward to cut tissue. The cutting element 506 may be rotated as the cutting element 506 is advanced which may increase the area cut by each of the cutting parts 508.

The cutting elements 506 also may occupy more than half of the cross-sectional area of the tubular element 502 which also helps to ensure complete separation from the surrounding tissue. By occupying at least half of the cross-sectional area, the cutting elements 506 may prevent the tissue from simply squeezing into the unoccupied space in the tubular element 502.

The tissue removal device 500 also has a transport element 510 which transports the tissue proximally. The tissue is transported proximally with the cutting parts 508 closed to retain the tissue in the transport element 510. A tissue handling element 512 takes the tissue from the transport element 510 and visually presents the tissue to the user through a window 528 (FIG. 41) which is preferably illuminated. FIGS. 46-50 illustrate operation of the tissue handling element 512. The tissue handling element 512 has a support member 514 and a first part 516 and a second part 518 each pivoting about pins 521 coupled to the support member 514. The first and second parts 516, 518 are biased towards the closed position of FIG. 41 by one or more springs 523. The first and second parts 516, 518 form a cylindrical recess 520 in which the tissue is deposited from the transport element 510. The recess 520 also helps to deform the cutting parts 508 back to their straightened shape as explained below.

Figure 46:
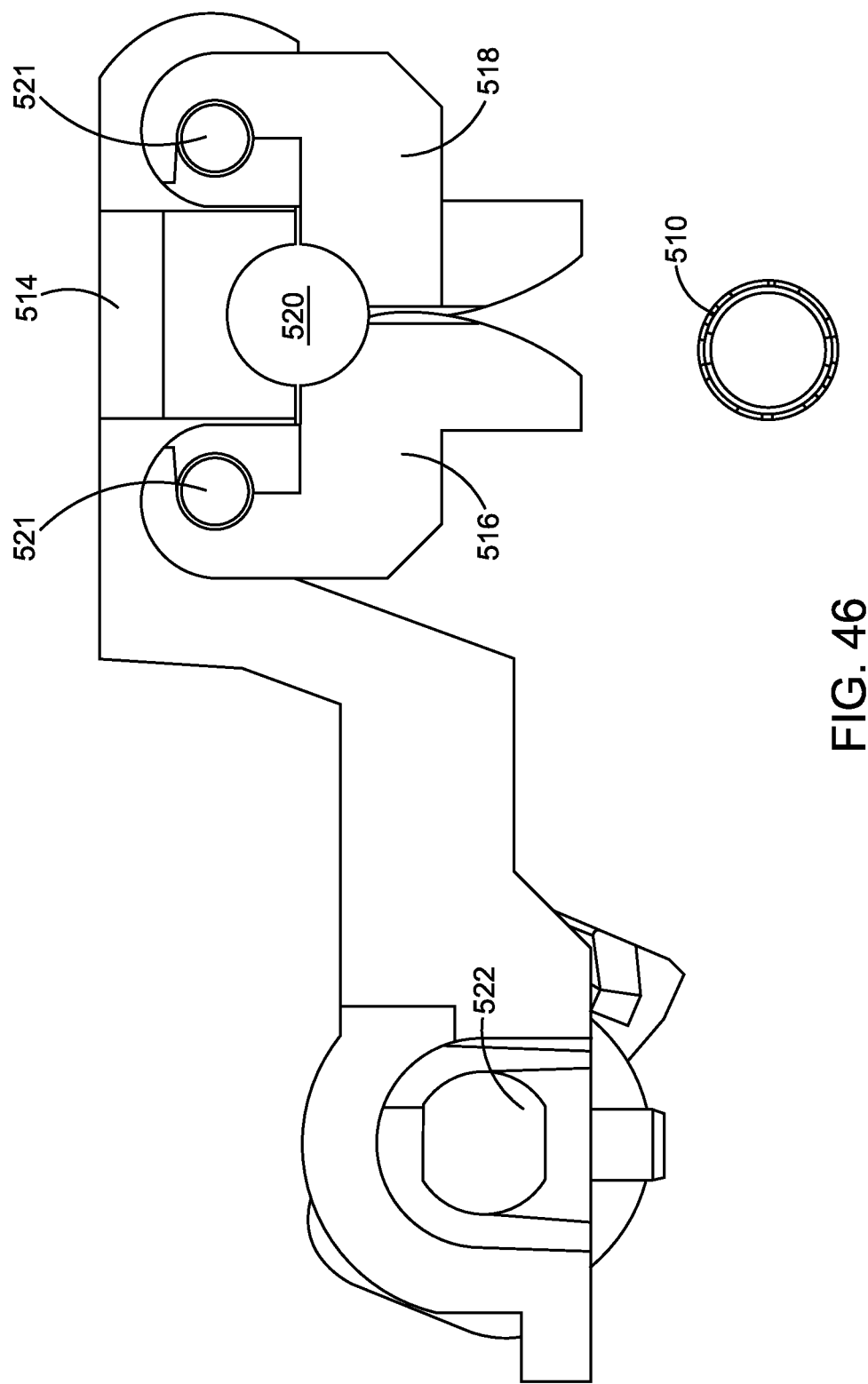
FIG. 46 is a side view of the tissue handling element and the transport element.
Figure 47:
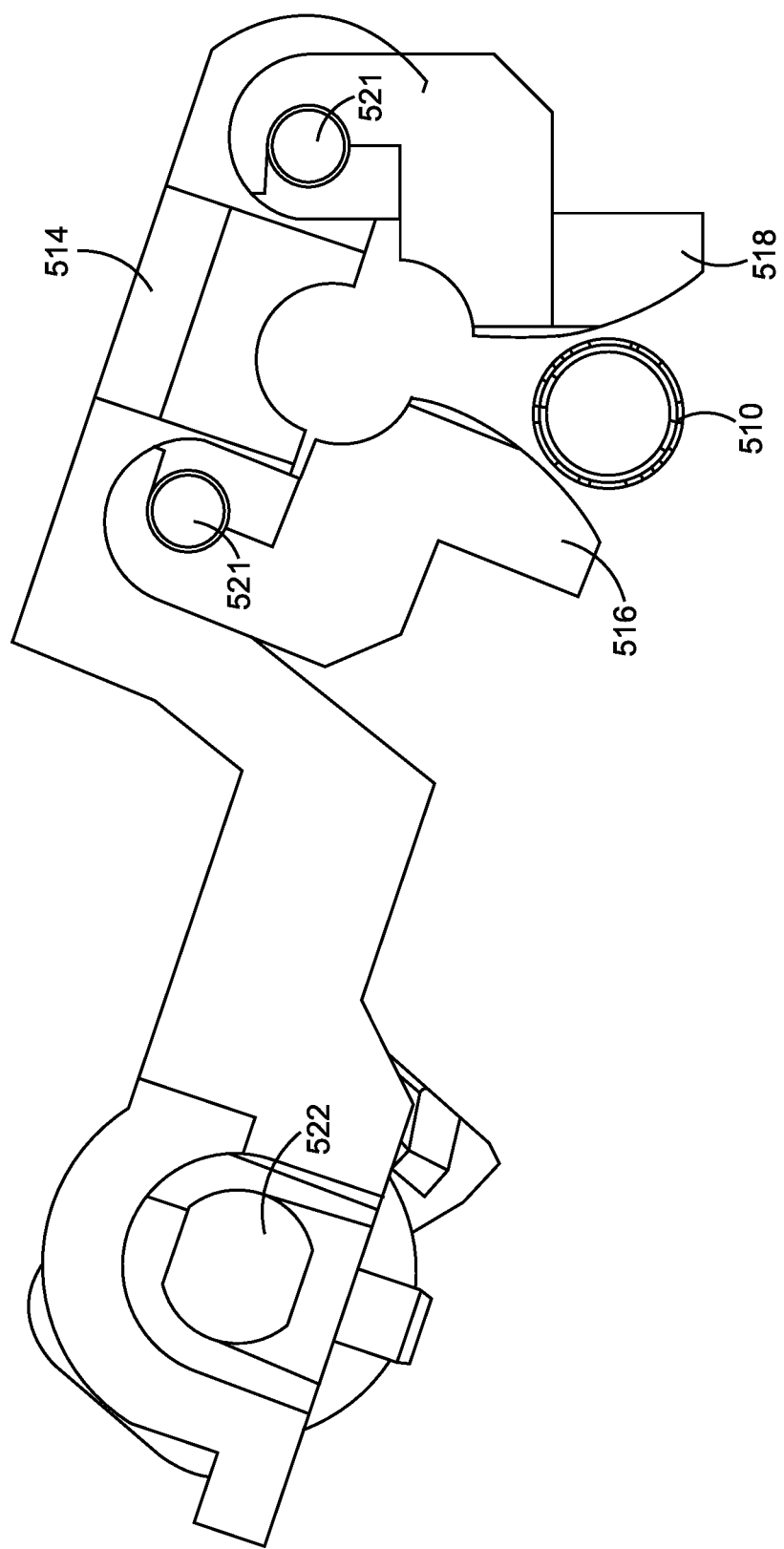
FIG. 47 is a side view of the tissue handling element moving toward the transport element.
Figure 48:
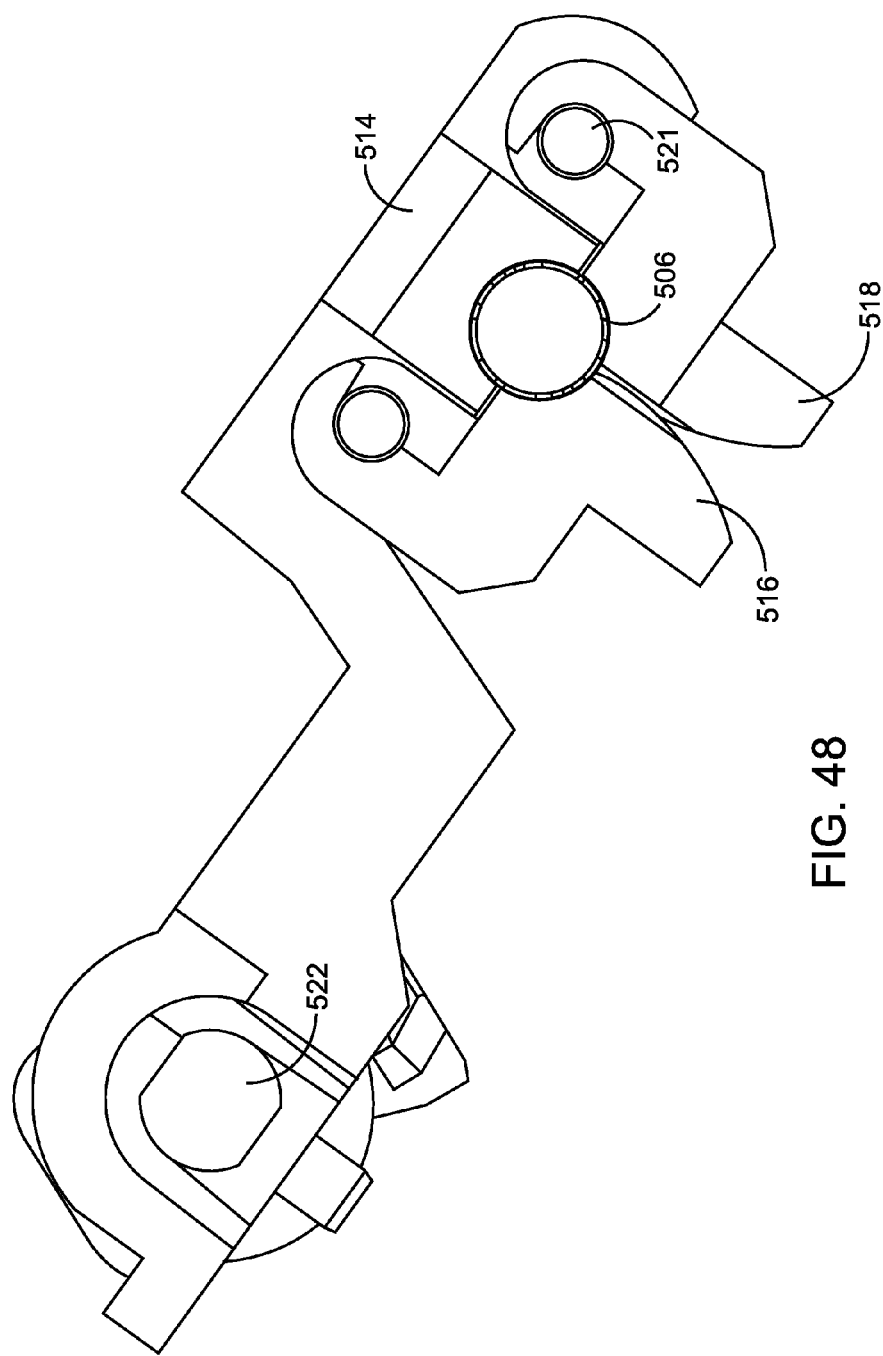
FIG. 48 is a side view of the tissue handling element forming a recess in which the transport element is positioned.
Figure 49:
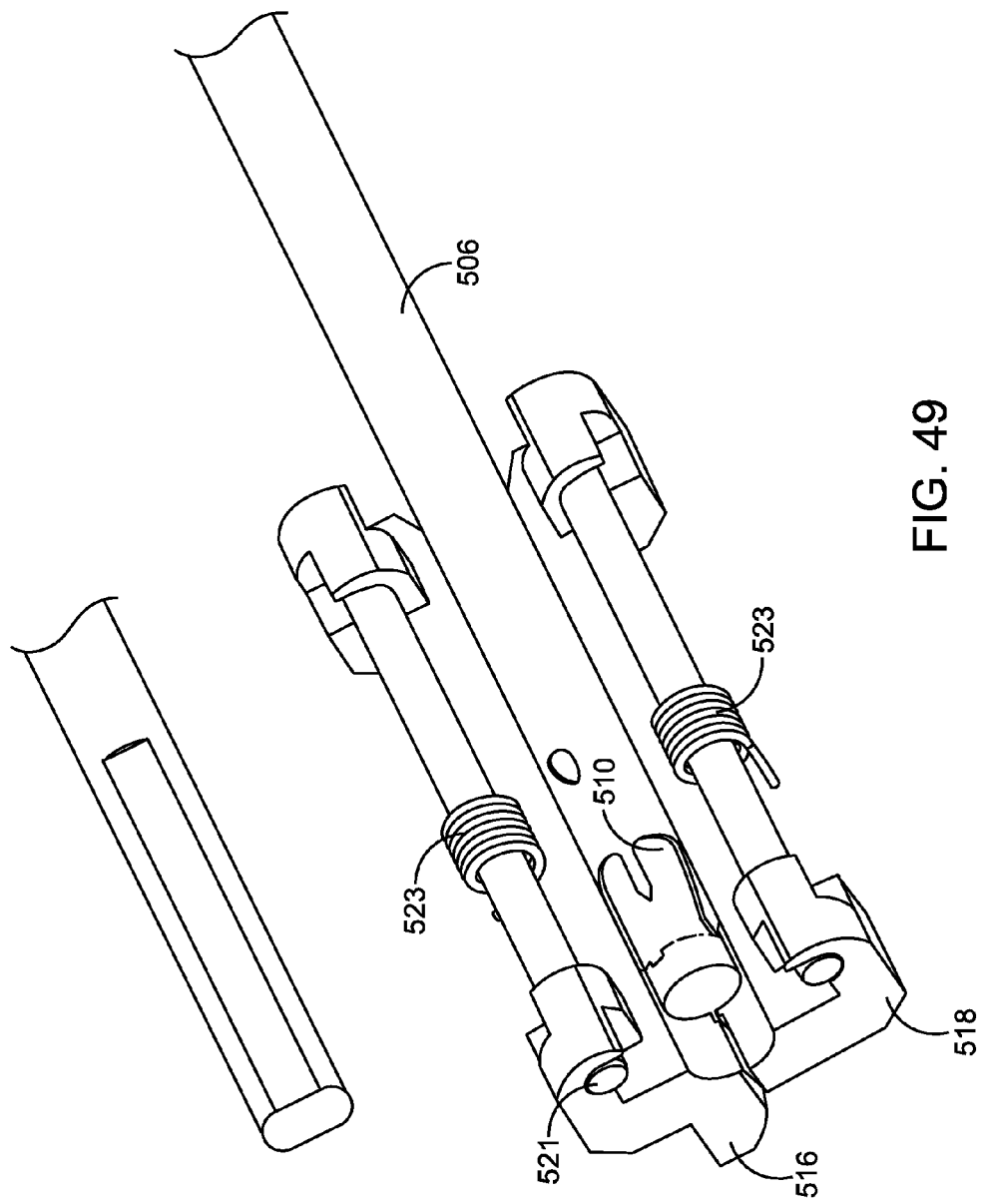
FIG. 49 is a perspective view of the tissue handling element with the support member omitted for clarity.

The support member 514 is coupled to an actuator 522 which rotates the support member 514 from the position of FIG. 46 toward the transport element 510 as shown in FIG. 47. FIG. 48 shows further rotation of the actuator 522 causes the first and second parts 516, 518 to form the recess 520 in which the transport element 510 is positioned. FIG. 49 shows the tissue handling element 512 with the support member 514 removed for clarity. Once the first and second parts 516, 518 are positioned around the transport element 510, the cutting element 506 may be withdrawn so that the cutting parts 508, which may be plastically deformed, are straightened as they are pulled between the transport element 510 and the cylindrical wall forming the recess 520. The transport element 510 and the cutting element 506 are then retracted from the cylindrical recess 520 thereby leaving the tissue within the tissue handling element 512. Similar to other embodiments, the device 500 may have an introducer 524 with a tip 526 of the introducer 524 being used to hold the tissue in place while the cutting element 506 and the transport element 510 are retracted as shown in FIG. 50.

Figure 41:
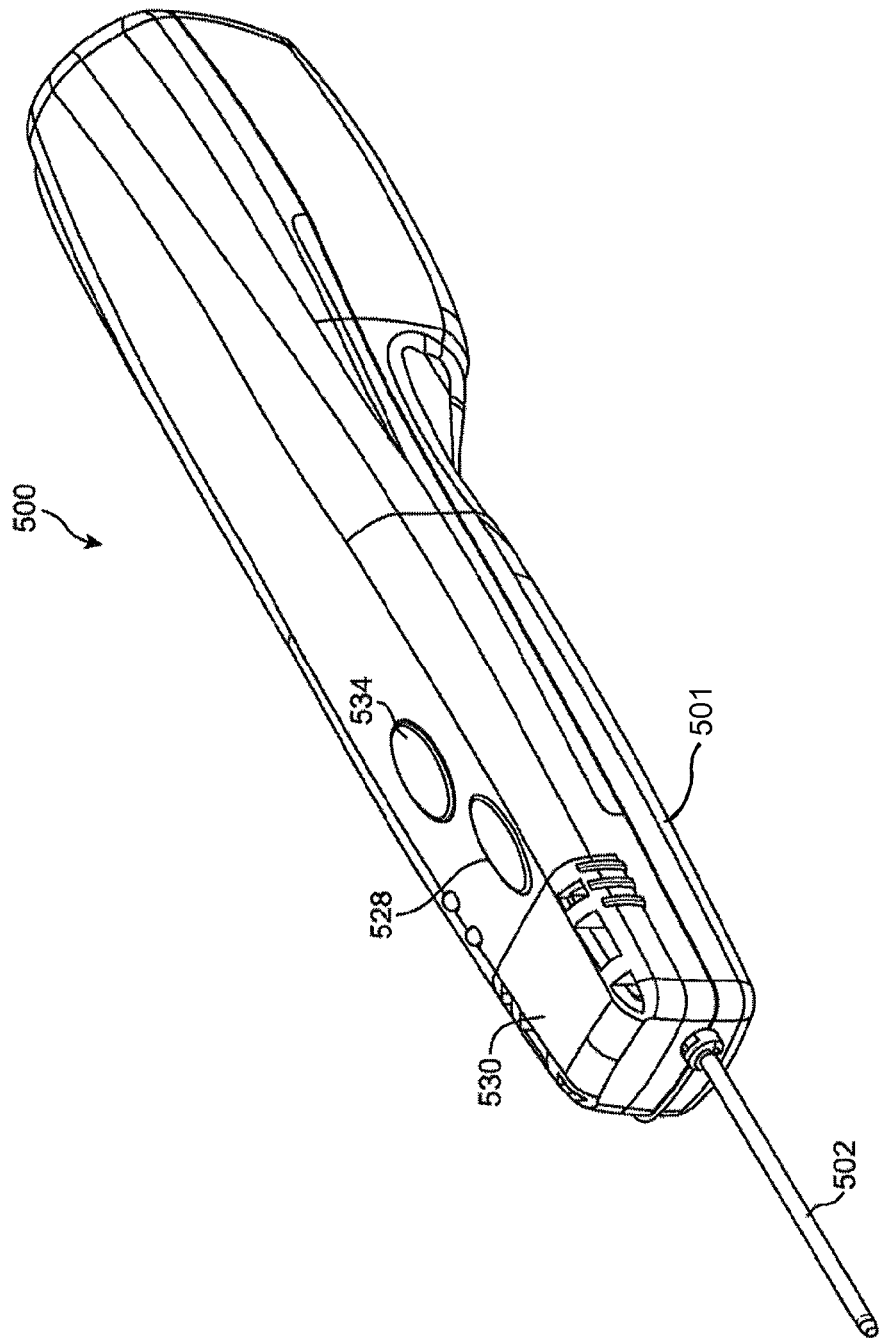
FIG. 41 shows another device for removing tissue from a patient.
Figure 42:
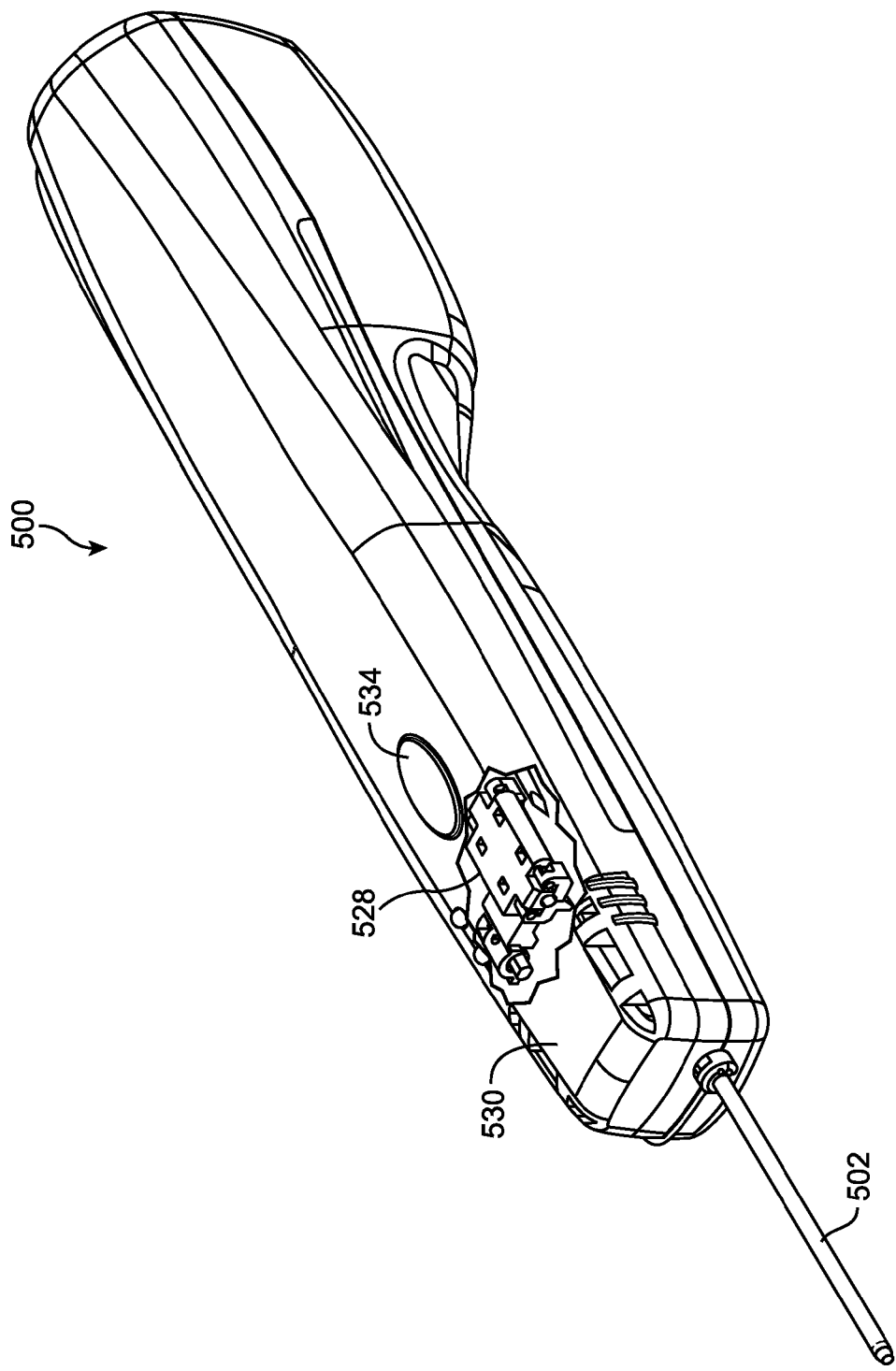
FIG. 42 shows a partial cut-away view of the device of FIG. 41 showing a tissue handling element which presents the tissue in a window for observation by the user.
Figure 43:
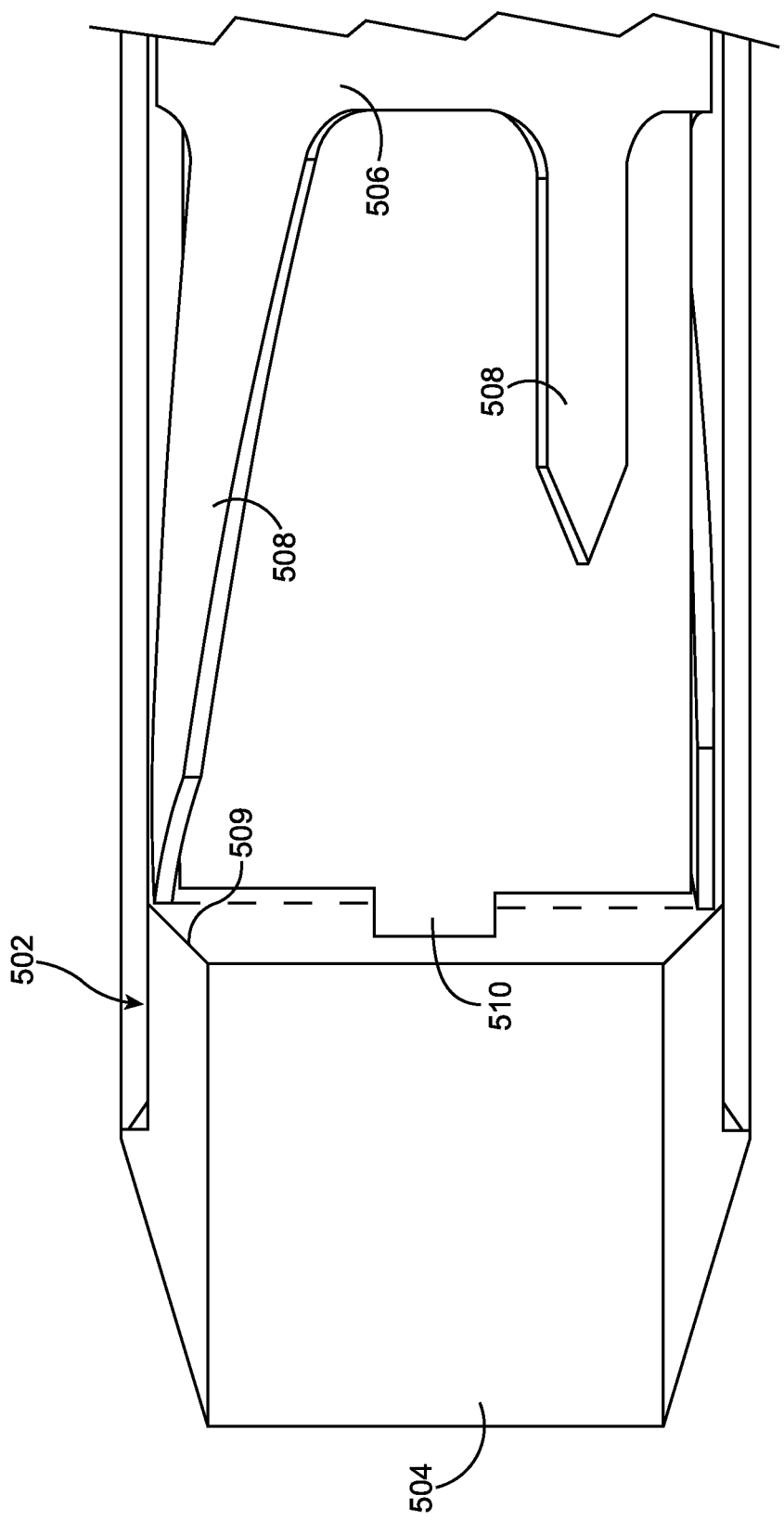
FIG. 43 shows a distal end of the device.
Figure 44:
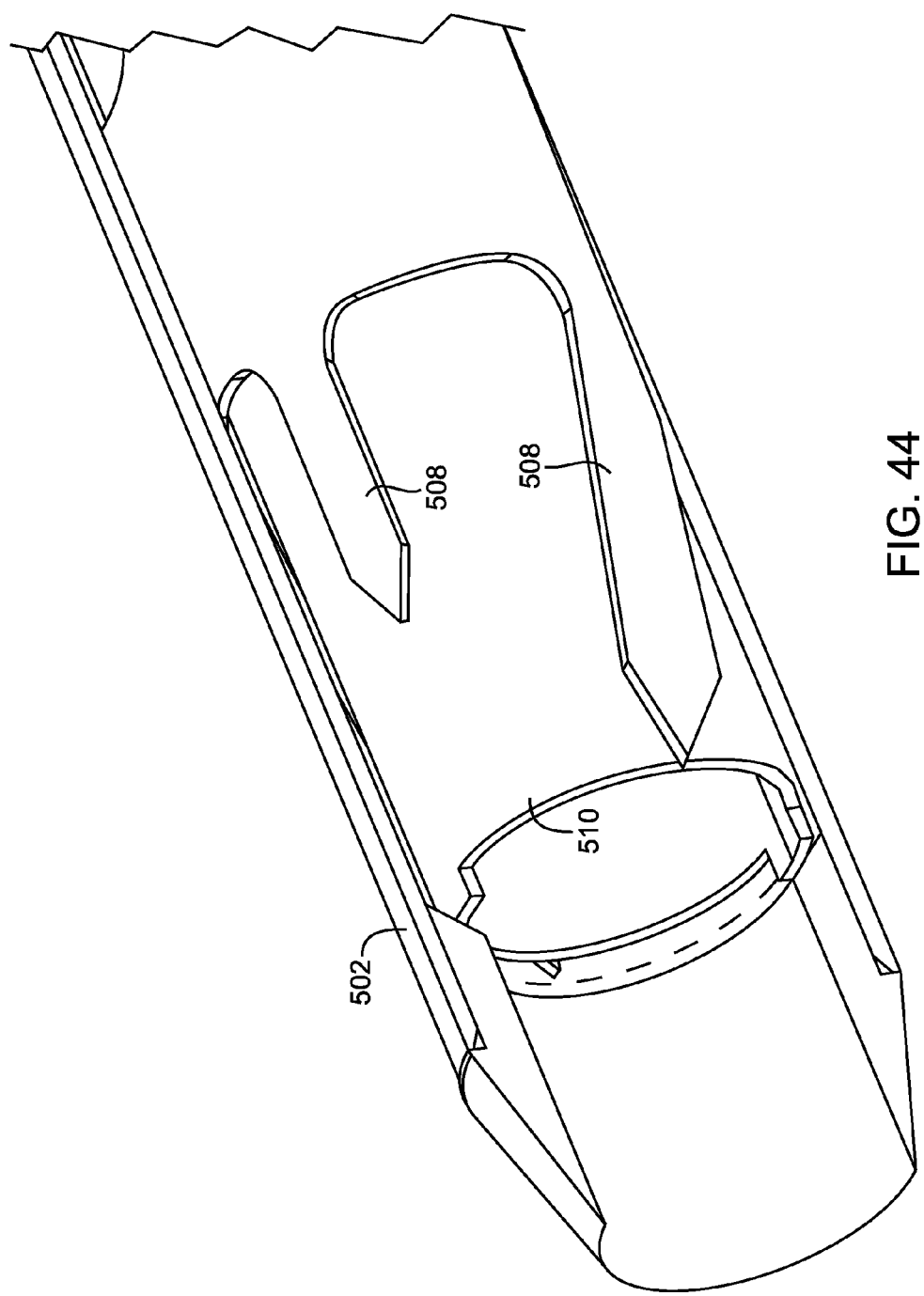
FIG. 44 is perspective partial cut-away of the distal end of the device.
Figure 45:
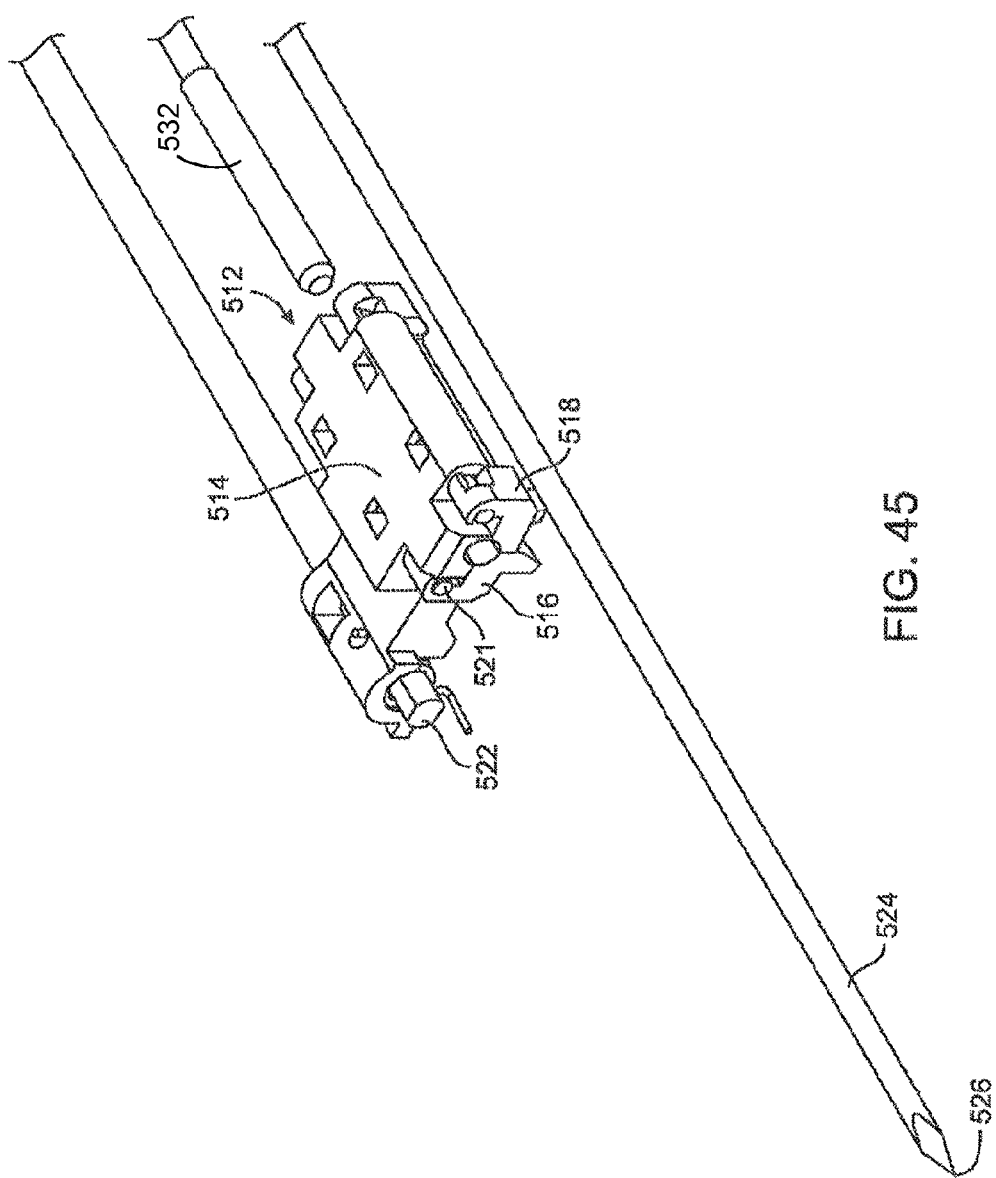
FIG. 45 shows the spatial relationship between the tissue handling element and the transport element.

The tissue handling element 512 is then rotated back to the position of FIG. 46 which positions the tissue beneath the window 528 (see FIG. 41). The support member 514 and window 528 are made of materials which permits the user to see the tissue lying beneath these elements and the area is preferably illuminated while the tissue is positioned in the window. A tissue chamber 530 has an opening (not shown) which receives the tissue when the tissue is pushed distally out of the recess by a pusher 532. The pusher 532 is coupled to the introducer 524 so that repositioning of the introducer 524 at the distal end of the tubular element 502 also causes the tissue to be moved into the tissue chamber. This procedure is carried out after the user actuates the device with a button 534 or the like. Thus, in one mode of operation the user depresses the button 534 a first time when it is desired to take a sample. The sample is taken with the introducer 524, tubular element 502, cutting element 506 and transport element 510 operating in any manner described herein. The tissue is then automatically displayed to the user at the window 528. Another press of the button 534 ejects the tissue and repositions the introducer 524 at the distal end so that the device 500 is ready to take more tissue. In another mode of operation, the device 500 may complete an entire work cycle with one push of the actuator rather than requiring two or more actuations. The operating cycle may include a brief pause for a few seconds while the tissue is displayed to the user as described herein.

The present invention has been described in connection with various preferred embodiments, however, it is understood that various modifications and alternative configurations are possible without departing from the scope of the invention. For example, the piercing element may be adhered to the tissue in any other suitable manner other than using the deployable anchor.

What is claimed is:

1. A device for removing tissue from a patient, comprising:
   a body;
   a tubular element coupled to the body and having an open end at a distal end, the tubular element defining a longitudinal axis, the tubular element being longitudinally movable relative to the body to an extended position, the tubular element configured to be driven into tissue to receive tissue through the open end when moving to the extended position;
   a tissue chamber coupled to the body;
   a transport element coupled to the body and being longitudinally movable relative to the tubular element, the transport element configured to contact the tissue which has entered the tubular element through the open end of the tubular element;
   a tissue handling element which is configured to receive the tissue from the transport element, the tissue handling element having a first part and a second part, the first and second parts being movable toward and away from the transport element, the first and second parts are movable toward one another and configured so that the tissue element is at least partially surrounded by the first and second parts; and a cutting element movable between a stored position and a cutting position, the cutting element moving toward the longitudinal axis when moving from the stored position to the cutting position.

2. The device of claim 1, wherein:

the tissue handling element is configured to receive the tissue from the transport element and display the tissue to the user.

3. The device of claim 1, wherein:

the transport element is withdrawn after the first and second parts are at least partially surrounding the transport element, wherein withdrawal of the transport element is configured to transfer the tissue from the transport element to the tissue handling element.

4. The device of claim 1, wherein:

the first and second parts are pivotably coupled to a support member, the first and second parts pivoting relative to one another when moving to at least partially surround the transport element.

5. The device of claim 1, wherein:

the transport element is movably coupled to the tubular element so that the transport element is advanced distally together with the tubular element when the tubular element moves to the extended position.

6. The device of claim 1, wherein:

the transport element also has an open end positioned proximal to the open end of the tubular element.

7. The device of claim 1, wherein:

the cutting element is also longitudinally movable within the tubular element, the cutting element remaining in the cutting position and moving proximally with the transport element when the transport element moves proximally toward the tissue chamber.

8. The device of claim 1, wherein:

the cutting element is positioned in an annular space between the tubular element and the transport element when in the stored position.

9. The device of claim 1, wherein:

at least one of the cutting element, the transport element and the tubular element rotate about the longitudinal axis when the cutting element moves from the stored position to the cutting position.

10. The device of claim 1, wherein:

the transport element has a sharp tip configured to penetrate the tissue being removed.

11. The device of claim 1, further comprising:

an introducer having a distal tip, the introducer being movable from an advancing position to a stored position, the distal tip extending beyond the open end of the tubular element when in the advancing position.

12. A device for removing tissue from a patient, comprising:

a body;

a tubular element coupled to the body and having an open end at a distal end, the tubular element defining a longitudinal axis, the tubular element being longitudinally movable relative to the body to an extended position, the tubular element configured to be driven into tissue to receive tissue through the open end when moving to the extended position;

a tissue chamber coupled to the body;

a transport element coupled to the body and being longitudinally movable relative to the tubular element, the transport element configured to contact the tissue which has entered the tubular element through the open end of the tubular element;

a tissue handling element configured to receive the tissue from the transport element, the tissue handling element having a first part and a second part, the first and second parts being movable toward and away from the transport element, the first and second parts are pivotably coupled to a support member, the first and second parts pivoting relative to one another when moving to at least partially surround the transport element; and a cutting element movable between a stored position and a cutting position, the cutting element moving toward the longitudinal axis when moving from the stored position to the cutting position.

\* \* \* \* \*